United States Patent

Barth et al.

Patent Number: 5,270,331
Date of Patent: Dec. 14, 1993

[54] PRODRUGS OF ANTIINFLAMMATORY 3-ACYL-2-OXINDOLE-1-CARBOXAMIDES

[75] Inventors: Wayne E. Barth, East Lyme; Kelvin Cooper, Noank; Edward F. Kleinman, Pawcatuck; Lawrence A. Reiter, Mystic; Ralph P. Robinson, Gales Ferry, all of Conn.

[73] Assignee: Pfizer, Inc., New York, N.Y.

[21] Appl. No.: 9,188

[22] Filed: Jan. 26, 1993

[51] Int. Cl.$^5$ .................. A61K 31/40; C07D 403/06
[52] U.S. Cl. .................. 514/414; 548/468; 548/406; 514/212; 514/227.5; 514/235.2; 514/323; 514/339; 540/602; 544/62; 544/144; 546/201; 546/273
[58] Field of Search ............ 514/414, 212, 227.5, 514/235.2, 323, 339; 548/468; 540/602; 544/62, 144; 546/201, 273

[56] References Cited

U.S. PATENT DOCUMENTS 4,556,672  12/1985  Kadin .................. 514/414
5,118,703   6/1992  Reiter et al. .......... 514/414

FOREIGN PATENT DOCUMENTS 0365194  4/1990  European Pat. Off. ...... 548/468

Primary Examiner—Joseph Paul Brust
Assistant Examiner—Jacqueline Haley
Attorney, Agent, or Firm—Peter C. Richardson; Gregg C. Benson; Mervin E. Brokke

[57] ABSTRACT

Antiinflammatory and analgesic oxindole prodrugs of the formula

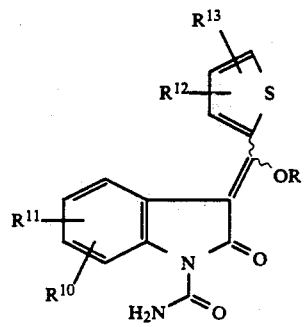

wherein $R^{10}$, $R^{11}$, $R^{12}$ and $R^{13}$ are hydrogen, alkyl or halogen and R is methyleneoxyalkanoyl, methyleneoxyalkenoyl or alkenoyl.

20 Claims, No Drawings

PRODRUGS OF ANTIINFLAMMATORY 3-ACYL-2-OXINDOLE-1-CARBOXAMIDES

The present invention is concerned with antiinflammatory and analgesic agents and, in particular, with enol esters and ether prodrugs of 3-acyl-2-oxindole-1-carboxamides, a class of known nonsteroidal antiinflammatory agents.

BACKGROUND OF THE INVENTION

The use of oxindoles as antiinflammatory agents has been reported in U.S. Pat. No. 3,634,453, and consisted of 1-substituted-2-oxindole-3-carboxamides. Recently, a series of 3-acyl-2-oxindole-1-carboxamides was disclosed in U.S. Pat. No. 4,556,672 to be inhibitors of the cyclooxygenase (CO) and lipoxygenase (LO) enzymes and to be useful as analgesic and antiinflammatory agents in mammalian subjects. Certain prodrugs of 3-acyl-2-oxindoles-1-carboxamides are described in commonly owned U.S. Pat. No. 5,118,703 which are of the formula:

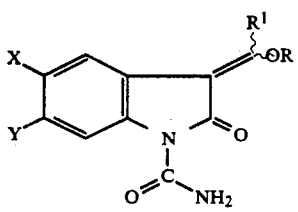

(A)

wherein X and Y are each hydrogen, fluoro or chloro; $R^1$ is 2-thienyl or benzyl; and R is alkanoyl of two to ten carbon atoms, cycloalkylcarbonyl of five to seven carbon atoms, phenylalkanoyl of seven to ten carbon atoms, chlorobenzoyl, methoxybenzoyl, thenoyl, omega-alkoxycarbonylalkanoyl said alkoxy having one to three carbon atoms and said alkanoyl having three to five carbon atoms; alkoxy carbonyl of two to ten carbon atoms; phenoxycarbonyl; 1-(acyloxy)alkyl said acyl having one to four carbon atoms and said alkyl having two to four carbon atoms; 1-(alkoxycarbonyloxy)alkyl said alkoxy having two to five carbon atoms and said alkyl having one to four carbon atoms; atoms. U.S. Pat. No. 5,118,703 and U.S. Pat. No. 4,556,672 are hereby incorporated by reference.

SUMMARY OF THE INVENTION

The present invention provides antiinflammatory ether and ester prodrugs of the formula

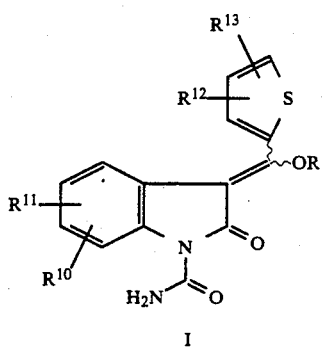

I wherein R is

-continued

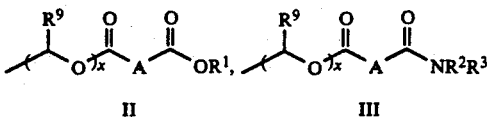

II           III

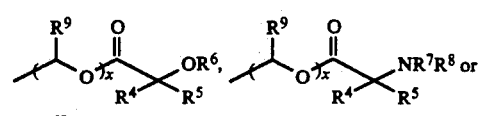

IV           V

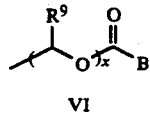

VI wherein x is 0 or 1;

A is a $C_1$-$C_5$ alkylene or $C_2$-$C_6$ alkenyl chain, optionally substituted with up to two substituents independently selected from $C_1$-$C_7$ alkyl or $C_3$-$C_7$ cycloalkyl; or $(CH_2)_nO(CH_2)_m$, where the methylene groups may be optionally substituted with up to two substituents independently selected from $C_1$-$C_7$ alkyl or $C_3$-$C_7$ cycloalkyl; or a $C_3$-$C_7$ cycloalkyl or cycloalkenyl group optionally substituted with up to two $C_1$-$C_3$ alkyl groups; or a 4-7 membered hetero-alicyclic group containing an O, S or $NR^6$ link; or a phenylene group optionally substituted with up to two substituents independently selected from $C_1$-$C_3$ alkyl, $C_1$-$C_3$ alkyloxy, halogen or $CF_3$;

B is a $C_2$-$C_6$ alkenyl phenyl, 2, 3 or 4-pyridyl, 2, 3 or 4-piperidinyl, 2 or 3-pyrrolidyl, $OCH_2CO_2R^1$ or $OCH_2CONR^2R^3$;

$R^1$ is H, $C_1$-$C_7$ alkyl, $C_3$-$C_7$ cycloalkyl, phenyl($C_1$-$C_4$)alkyl, $(CH_2)_pCO_2R^2$, or $(CH_2)_pCONR^2R^3$;

or $R^1$ may form with A a 5, 6 or 7 membered lactone ring optionally substituted with a $C_1$-$C_3$ alkyl group;

$R^2$ and $R^3$ are independently H, $C_1$-$C_7$ alkyl, $C_3$-$C_7$ cycloalkyl, phenyl($C_1$-$C_4$)alkyl; or $R^2$ and $R^3$, when taken together with the attached nitrogen, may represent a pyrrolidine, piperidine, morpholine or homopiperidine group optionally substituted with up to two $C_1$-$C_3$ alkyl groups; or $R^2$ or $R^3$ may form with A, a 5, 6 or 7 membered lactam ring, optionally substituted with up to two $C_1$-$C_3$ alkyl groups;

$R^4$ and $R^5$ are independently H, $C_1$-$C_7$ alkyl $C_3$-$C_7$ cycloalkyl, phenyl($C_1$-$C_4$)alkyl, $(CH_2)_pCO_2R^2$, $(CH_2)_pCONR^2R^3$, $(CH_2)_pNR^7R^8$, $(CH_2)_pOR^6$ or $(CH_2)_pSR^6$; or $R^4$ and $R^5$ when taken together represent a $C_3$-$C_7$ cycloalkyl ring, optionally substituted with up to two $C_1$-$C_3$ alkyl groups;

$R^6$ is H, $C_1$-$C_6$ alkyl, $(CH_2)_pCOOR^2$, $C_3$-$C_7$ cycloalkyl optionally substituted with up to two $C_1$-$C_6$ alkyl groups, phenyl($C_1$-$C_4$)alkyl optionally substituted on the phenyl ring with up to two substituents independently selected from $C_1$-$C_3$ alkyl, $C_1$-$C_3$ alkoyloxy, halogen or $CF_3$, $COR^2$, $CONR^2R^3$, or a phenyl group optionally substituted with up to two substituents independently selected from $C_1$-$C_3$ alkyl, $C_1$-$C_3$ alkyloxy, halogen or $CF_3$; or when taken with $R^4$ and the attached oxygen, may represent an oxetan, tetrahydrofuran, tetrahydropyran or oxepan ring optionally substituted with up to two $C_1$–$C_3$ alkyl groups;

$R^7$ and $R^8$ are independently H, $C_1$–$C_6$ alkyl, $C_3$–$C_7$ cycloalkyl, phenyl($C_1$–$C_4$)alkyl, $COR^2$, $COOR^2$; or independently $C_2$–$C_7$ alkanoyl, $C_4$–$C_8$ cycloalkanoyl, optionally substituted with up to two substituents independently selected from $C_1$–$C_6$ alkyl, $C_3$–$C_7$ cycloalkyl, phenyl($C_1$–$C_4$)alkyl, $C_3$–$C_7$ branched alkyl; or $R^7$ and $R^8$ when taken together with the attached nitrogen may represent a pyrrolidine, piperidine or homopiperidine group optionally substituted with up to two substituents independently selected from $C_1$–$C_6$ alkyl, $C_3$–$C_7$ cycloalkyl, $C_3$–$C_7$ branched alkyl, or oxo;

$R^9$ is H or methyl;

$R^{10}$, $R^{11}$, $R^{12}$ and $R^{13}$ are independently selected from hydrogen, $C_1$–$C_4$ alkyl and halogen;

m and n are independently 0, 1 or 2 where either m or n must be at least 1; and p is 1 to 3.

Particularly preferred are compounds of formula I wherein one of $R^{10}$ and $R^{11}$ is 5-fluoro and the other is 6-chloro.

A second preferred group of compounds are those of formula I wherein one of $R^{10}$ and $R^{11}$ is 5-fluoro and the other is 6-chloro and R is formula II, wherein x is 0, A is a $C_2$–$C_6$ alkenyl chain and $R^1$ is hydrogen. Especially preferred within this group are compounds where A is —CH=CH— with E geometry and $R^{12}$ and $R^{13}$ are hydrogen. Also preferred within this group are compounds where x is 1, A is alkylene and $R^1$ is benzyl.

A third preferred group of compounds are those of formula I where one of $R^{10}$ and $R^{11}$ is 5-fluoro and the other is 6-chloro and R is formula IV and x is 1. Especially preferred within this group are compounds where $R^4$, $R^9$, $R^{12}$ and $R^{13}$ are hydrogen, $R^5$ is hydrogen, methyl or ethyl and $R^6$ is hydrogen, methyl, benzyl or $CH_2COOR^2$.

A fourth preferred group of compounds are those of formula I where one of $R^{10}$ and $R^{11}$ is 5-fluoro and the other is 6-chloro, x is 1 and R is formula V. Preferred within this group are compounds where $R^4$, $R^9$, $R^7$, $R^8$, $R^{12}$ and $R^{13}$ are hydrogen, and $R^5$ is $(CH_2)_p NR^7R^8$, methyl or benzyl. Also preferred within this group are compounds where $R^7$ is $COR^2$.

A fifth preferred group of compounds are those of formula I where one of $R^{10}$ and $R^{11}$ is 5-fluoro and the other is 6-chloro, x is 1, R is formula VI and B is 2- or 3-pyrrolidine.

The present invention also comprises a method for treating inflammation in a mammal which comprises administering to said mammal an antiinflammatory effective amount of a compound selected from those of formula (I).

The present invention further comprises a method for treating pain in a mammal which comprises administering to said mammal an analgesic effective amount of a compound selected from those of formula (I).

DETAILED DESCRIPTION OF THE INVENTION

The enol ethers and esters of the present invention are not enolic acids as are the parent compounds and have the potential to show reduced gastric irritation when compared to said parent compounds.

The term "prodrug" refers to compounds which are drug precursors which, following administration and absorption, release the drug in vivo via some metabolic process.

While all of the usual routes of administration are useful with the invention compounds, the preferred route of administration is oral. After gastrointestinal absorption the present compounds are hydrolyzed in vivo to the corresponding compounds of formula (I) where R is hydrogen, or a salt thereof. Since the prodrugs of the invention are not enolic acids, exposure of the gastrointestinal tract to acidic parent compound is thereby minimized. Further, since gastrointestinal complications have been noted as a major adverse reaction of acid non-steroidal antiinflammatory drugs [see e.g., DelFavero in "Side Effects of Drugs Annual 7", Dukes and Elis, Eds. Excerpta Medica, Amsterdam, 1983, p. 104–115], the invention compounds (I) are likely to have a distinct advantage over the parent enolic compounds.

In converting the 3-acyl-2-oxindole-1-carboxamides to the compounds of formula I, the substituents on the exocyclic double bond at the 3-position can by syn, anti or a mixture of both. Thus, the compounds of the structures

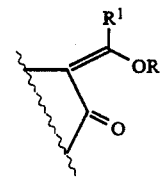

and

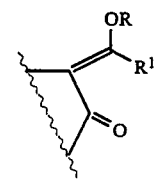

or mixtures thereof are depicted as

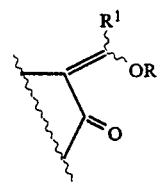

All forms of these isomers are considered part of the present invention.

The 3-acyl-2-oxindole-1-carboxamides required as starting materials are available by methods well known in the art, see, for example, U.S. Pat. Nos. 3,634,453 and 4,556,672. The other starting reagents noted above are available commercially, or are prepared by well known methods, or are described in the preparation section hereinbelow.

The preparation of the compounds of the present invention is readily achieved. A salt of the appropriate 3-acyl-2-oxindole-1-carboxamide is formed in a reaction inert solvent and used with or without isolation in a subsequent reaction with an acid halide or α haloalkyl ester. Conditions of these reactions are not critical; temperature may vary from about 0° C. to about 50° C.

with a preferred range being about 0° C. to about 20° C. The reaction time will vary with the selected reactants and temperature, but ranges from about 8 to 90 hours with the preferred time being about 20 hours.

The salt of the 3-acyl-2-oxindole-1-carboxamide may be alkali metal, tertiary amine or quaternary ammonium. Alkali metals include lithium, sodium and potassium. Tertiary amines are generally low molecular weight aliphatic amines such as trimethylamine, triethylamine, tributylamine and mixed animes such as diisopropylethylamine, diethyl aminopyridine; and heterocyclic amines such as pyridine and N-methylmorpholine. Quaternary ammonium compounds may be symmetrical or mixed alkyl amines of straight or branched chains. Sodium, diisopropylethylamine, triethylamines and tetrabutylammonium salts are preferred.

The acid halide may be the chloride or bromide; the chloride is preferred. Alpha halo esters may be chloro, bromo or iodo esters with chloro and iodo being preferred. The chloro ester is preferably used with sodium iodide, thus generating the iodo ester in situ.

Bioavailability of the prodrugs of the present invention was determined by comparison of the prodrug to the parent compound.

For example 3-[hydroxy-2(thienyl)methylene]-6-chloro-5-fluoro-2,3-dihydro-2-oxo-1H-indole-1-carboxamide and selected prodrugs were orally administered to fasted male Sprague-Dawley rats at dose levels of 3 mg equivalents 3-[hydroxy-2(thienyl)methylene]-6-chloro-5-fluoro-2,3-dihydro-2-oxo-1H-indole-1-carboxamide/kg as a solution or suspension in 0.1% methylcellulose. Dosing volumes of each drug formulation were maintained at 1 mL per 1 kg bodyweight. Following oral administration, blood samples were obtained by retroorbital sinus bleeding into heparinized tubes at 1,3 and 6 hours post-dose and immediately chilled. Plasma was stored at $-20°$ C. until analysis.

Plasma concentrations of 3-[hydroxy-2(thienyl)methylene]-6-chloro-5-fluoro-2,3-dihydro-2-oxo-1H-indole-1-carboxamide following administration of 3-[hydroxy-2(thienyl)methylene]-6-chloro-5-fluoro-2,3-dihydro-2-oxo-1H-indole-1-carboxamide and prodrugs were determined by high pressure liquid chromatography with ultraviolet detection at 360 nm. The lower limit of quantitation for 3-[hydroxy-2(thienyl)methylene]-6-chloro-5-fluoro-2,3-dihydro-2-oxo-1H-indole-1-carboxamide was 0.2 $\mu$g/mL.

Area under the concentration vs. time curve [AUC(0-6 hr)] were determined by the linear trapezoidal method for 3-[hydroxy-2(thienyl)methylene]-6-chloro-5-fluoro-2,3-dihydro-2-oxo-1H-indole-1-carboxamide following oral administration of 3-[hydroxy-2(thienyl)-methylene]-6-chloro-5-fluoro-2,3-dihydro-2-oxo-1H-indole-1-carboxamide and each prodrug. Relative bioavailability for 3-[hydroxy-2(thienyl)methylene]-6-chloro-5-fluoro-2,3-dihydro-2-oxo-1H-indole-1-carboxamide following administration of each prodrug was assessed by determining the ratio of the 3-[hydroxy-2(thienyl)methylene]-6-chloro-5-fluoro-2,3-dihydro-2-oxo-1H-indole-1-carboxamide AUC(0-6) value following administration of prodrug to the 3-[hydroxy-2(thienyl)methylene]-6-chloro-5-fluoro-2,3-dihydro-2-oxo-1H-indole-1-carboxamide AUC(0-6) value following administration of 3-[hydroxy-2(thienyl)methylene]-6-chloro-5-fluoro-2,3-dihydro-2-oxo-1H-indole-1-carboxamide.

The prodrugs of formula (I) are evaluated for their antiinflammatory and analgesic activity according to known methods such as the rat foot edema test, rat adjuvant-induced arthritis test or phenylbenzoquinone-induced writhing test in mice, as previously used in the evaluation of the parent compounds and described in the references cited above and elsewhere in the literature; see e.g., C. A. Winter, in "Progress in Drug Research" edited by E. Jucker, Birkhauser Verlag, Basel, Vol. 10, pp. 139–192 (1966).

On a molar basis, the present prodrugs are generally dosed at the same level and frequency as the known 3-acyl-2-oxindole-1-carboxamides from which they are derived. However, the non-enolic nature of the present compounds should generally permit higher tolerated oral doses, when such higher dosage is required in the control of pain and inflammation.

The present prodrugs are also formulated in the same manner, and administered by the same routes as the known parent compounds, as described in the above cited references. The preferred route of administration is oral, thus taking particular advantage of the non-enolic nature of the present compounds.

The present invention is illustrated by the following examples, but is not limited to the specific details of these examples.

EXAMPLE 1

6-Chloro-5-fluoro-2,3-dihydro-3[(4-methoxybenzoyl)oxy-(2-thienyl)methylene]-2-oxo-1-H-indole-1-carboxamide 3-[Hydroxy-2(-thienyl)methylene]-6-chloro-5-fluoro-2,3-dihydro-2-oxo-1H-indole-1-carboxamide (5.08 g, 15.0 mmole) was slurried in $CH_2Cl_2$ and treated with triethylamine (1.67 g, 16.5 mmole). This yellow solution was chilled in an ice water bath and treated with 4-methoxybenzoyl chloride (12.8 g, 75.0 mmole) in one portion. After 18 hr. the reaction mixture was filtered to remove a yellow precipitate. The filtrate was diluted with additional $CH_2Cl_2$ and washed with 1N HCl (2×) and saturated $NaHCO_3$/brine mixture. After drying with $MgSO_4$, filtration, concentration and chasing with ethanol (2×), a solid was obtained which was triturated with EtOAc/hexane. This was collected, combined with the solid that was directly removed from the reaction mixture and the whole recrystallized from EtOAc/hexane (4/1) and some acetone yielding 1.81 g (26%) of the desired product as yellow crystals: mp 220°–221° C.; Anal. calculated for $C_{22}H_{14}ClFN_2O_5S$: C, 55.88; H, 2.98; N, 5.92. Found: C, 56.04; H, 2.82; N, 5.88.

EXAMPLE 2

6-Chloro-5-fluoro-2,3-dihydro-3[(cinnamoyl)oxy-(2-thienyl)methylene]-2-oxo-1-H-indole-1-carboxamide The title compound was prepared by the procedure of Example 1 with the exception that cinnamoyl chloride was used: mp 214°–215° C.; Anal. calculated for $C_{23}H_{14}ClFN_2O_4S$: C, 58.91; H, 3.01; N, 5.97. Found: C, 58.52; H, 2.89; N, 5.91.

EXAMPLE 3

6-Chloro-5-fluoro-2,3-dihydro-3-[(3-methoxybenzoyl)oxy-(2-thienyl)methylene]-2-oxo-1H-indole-1-carboxamide The title compound was prepared by the procedure of Example 1 with the exception that 3-methoxybenzoyl chloride (4 equiv.) was used and chloroform was the solvent. The product was recrystallized from isopropyl alcohol: mp 196°-220°. The $^1$H NMR spectrum indicated the sample contained both the E and Z geometrical isomers of the title compound in a ratio of 17:83. Anal. calculated for $C_{22}H_{14}ClFN_2O_5S$: C, 55.88; H, 2.98; N, 5.92. Found: C, 56.00; H, 2.82; N, 5.78.

EXAMPLE 4

6-Chloro-5-fluoro-2,3-dihydro-3-[(2-methoxybenzoyl)oxy-(2-thienyl)methylene]-2-oxo-1H-indole-1-carboxamide The title compound was prepared by the procedure of Example 1 with the exception that 2-methoxybenzoyl chloride was used and chloroform was the solvent. The crude product was purified by flash chromatography on silica gel (eluting with 95:5 CHCl$_3$/MeOH) followed by recrystallization from isopropyl alcohol: mp 219°-221°. The $^1$H NMR spectrum indicated the sample contained only the E geometrical isomer of the title compound. Anal. calculated for $C_{22}H_{14}ClFN_2O_5S$: C, 55.88; H, 2.98; N, 5.92. Found: C, 55.32; H, 3.01; N, 5.66.

EXAMPLE 5

6-Chloro-5-fluoro-2,3-dihydro-3-[nicotinoyloxy-(2-thienyl)methylene]2-oxo-1H-indole-1-carboxamide The title compound was prepared by the procedure of Example 1 with the exception that nicotinoyl chloride (2.5 equiv.) and 3.4 equiv. of triethylamine were used and chloroform was the solvent. The crude product was purified by flash chromatography (using 83:17 CHCl$_3$/MeOH as eluant) followed by recrystallization from isopropyl alcohol: mp 201°-202.5°. Anal. calculated for $C_{20}H_{11}ClFN_3O_4S$: C, 54.12; H, 2.50; N, 9.47. Found: C, 54.01; H, 2.46; N, 9.30.

EXAMPLE 6

6-Chloro-5-fluoro-2,3-dihydro-3-[isonicotinoyloxy-(2-thienyl)methylene]-2-oxo-1H-indole-1-carboxamide The title compound was prepared by the procedure of Example 1 with the exception that isonicotinoyl chloride (1:1 equiv.) and diisopropylethylamine (2 equiv.) were used. The product, obtained directly by filtration of the reaction mixture, was recrystallized from isopropyl alcohol: mp 219.5°-221°. Anal. calculated for $C_{20}H_{11}ClFN_3O_4S$: C, 54.12; H, 2.50; N, 9.47. Found: C, 54.11; H, 2.43; N, 9.32.

EXAMPLE 7

6-Chloro-5-fluoro-2,3-dihydro-3-[picolinoyloxy-(2-thienyl)methylene]-2-oxo-1H-indole-1-carboxamide The title compound was prepared by the procedure of Example 1 with the exception that picolinoyl chloride (1.1 equiv.) and diisopropyl-ethylamine (2 equiv.) were used. The product, obtained directly by filtration of the reaction mixture, was recrystallized from isopropyl alcohol: mp 184°-185°. Anal. calculated for $C_{20}H_{11}ClFN_3O_4S$: C, 54.12; H, 2.50; N, 9.47. Found: C, 53.73; H, 2.34; N, 9.31.

EXAMPLE 8

6-Chloro-5-Fluoro-2-3-dihydro-3-[3-(ethyloxycarbonyl)propenoyloxy-(2-thienyl)methylene]-2-oxo-1H-indole-1-carboxamide a) 3-(Ethyloxycarbonyl)propenoyl chloride was prepared according to the procedure of Lutz (J. Am. Chem. Soc., 1930, 52, 3430).

b) The title compound was prepared by the procedure of Example 1 with the exception that 3-(ethyloxycarbonyl)propenoyl chloride (2 equiv.) and diisopropylethylamine were used. The crude product was purified by flash chromatography (eluting with CHCl$_3$ and then 98:2 CHCl$_3$/MeOH) followed by recrystallization from isopropanol: mp 165.5°-168°. The $^1$H NMR spectrum indicated the sample to contain both the E and Z geometrical isomers of the title compound in a ratio of 22:78. Anal calculated for $C_{20}H_{14}ClFN_2O_6S$: C, 51.68: H, 3.04; N, 6.03. Found: C, 51.42; H, 3.08; N, 5.86.

EXAMPLE 9

6-Chloro-5-fluoro-2,3-dihydro-3-[3-(methyloxycarbonyl)propenoyloxy-(2-thienyl)methylene]-2-oxo-1H-indole-1-carboxamide a) 3-(Methyloxycarbonyl)propenoyl chloride was prepared according to the procedure of Lutz (J. Am. Chem. Soc., 1930, 52, 3430).

b) The title compound was prepared by the procedure of Example 1 with the exception that 3-(methyloxycarbonyl)propenoyl chloride (2 equiv.) and diisopropylethylamine were used. The crude product was purified by flash chromatography (eluting with 95:5 CH$_2$Cl$_2$/iPrOH) followed by recrystallization from isopropanol: mp 183.5°-186°. The $^1$H NMR spectrum indicated the sample to contain both the E and Z geometrical isomers of the title compound in a ratio of 34:66. Anal. calculated for $C_{19}H_{12}ClFN_2O_6S$: C, 50.62; H, 2.68; N, 6.21. Found: C, 50.56; H, 2.84; N, 6.04.

EXAMPLE 10

6-Chloro-5-fluoro-2,3-dihydro-3-[benzyloxyacetyloxy-(2-thienyl)methylene]-2-oxo-1H-indole-1-carboxamide The title compound was prepared by the procedure of Example 1 with the exception that benzyloxyacetyl chloride (2 equiv.) and diisopropylethylamine (2 equiv.) were used. The crude product was purified by flash chromatography (eluting with CHCl$_3$) and followed by recrystallization from isopropyl alcohol: mp 150°-175°. Anal. calculated for $C_{23}H_{16}ClFN_2O_5S$: C, 56.74; H, 3.31; N, 5.75. Found: C, 58.41; H, 3.17; N, 5.00.

EXAMPLE 11

6-Chloro-5-fluoro-2,3-dihydro-3-[4-(benzyloxycarbonyl)benzoyloxy-(2-thienyl)methylene]-2-oxo-1H-indole-1-carboxamide The title compound was prepared by the procedure of Example 1 with the exception that 4-(benzyloxycarbonyl)benzoyl chloride (1.5 equiv.) and diisopropylethylamine (1.5 equiv.) were used. The crude product was purified by trituration with CHCl$_3$: mp 212°-218°. Anal. calculated for $C_{29}H_{18}ClFN_2O_6S$: C, 60.37; H, 3.14; N, 4.85. Found: C, 60.94; H, 3.00; N, 4.27.

EXAMPLE 12

6-Chloro-5-fluoro-2,3-dihydro-3-[3-carboxypropenoyloxy-(2-thienyl)methylene]-2-oxo-1H-indole-1-carboxamide a) 3-(2-Trimethylsilylethyloxycarbonyl)propenoyl chloride was prepared according to a modification of the procedure of Lutz (J. Am. Chem. Soc., 1930, 52, 3430) in which remaining fumaryl chloride and unwanted diester are removed by distillation under vacuum leaving the desired acid chloride behind in the pot.

b) The title compound was prepared by the procedure of Example 1 with the exception that 3-(2-trimethylsilylethyl-oxycarbonyl)propenoyl chloride (1.3 equiv.) and diisopropylethylamine were used. The crude product was purified by flash chromatography (using $CH_2Cl_2$, 99:1 $CH_2Cl_2$/MeOH and then 98:2 $CH_2Cl_2$/MeOH as eluants) followed by recrystallization from acetonitrile.

c) Hydrogen fluoride/pyridine complex (500 g) was cooled in an ice bath in a polyethylene bottle. The 3-(2-trimethylsilylethyloxycarbonyl)propenoyl derivative (33.84 g, 63 mmol) was then added 2-3 g portions. When the addition was complete, the resulting slurry was agitated in the cold for 0.5 hr. The reaction was then quenched by addition of $H_2O$. After drying in vacuo, the product was purified by trituration with hot ethyl acetate. The yield was 19.8 g. An analytical sample was obtained by recrystallization of a small sample from acetic acid: mp 229°–232°. The $^1H$ NMR spectrum indicated the sample to contain only the E geometrical isomer of the title compound. Anal. calculated for $C_{18}H_{10}ClFN_2O_6S$: C, 49.50; H, 2.31; N, 6.41. Found: C, 49.23; H, 2.23; N, 6.37.

EXAMPLE 13

6-Chloro-5-fluoro-2,3-dihydro-3-[3-carboxybenzoyloxy-(2-thienyl)methylene]-2-oxo-1H-indole-1-carboxamide a) A solution of isophthaloyl dichloride (40.6 g, 200 mmol) and 2,2,2-trichloroethanol (30.9 g, 207 mmol) in toluene was heated at reflux for 24 hr. The solvent was evaporated and the remaining material was distilled under vacuum. The desired product distilled over along with some of the unwanted bis(2,2,2-trichloroethyl)ester between 125° and 170° at 0.2 mm Hg. On standing, this unwanted side product separated out as a solid. The desired product, 3-(2,2,2-trichloroethyloxycarbonyl)benzoyl chloride (19.0 g) was decanted off for use in the next step.

b) The title compound was prepared by the procedure of Example 1 with the exception that 3-(2,2,2-trichloroethyloxycarbonyl)benzoyl chloride (2 equiv.) and diisopropylethylamine (2 equiv.) were used. The product, obtained directly by filtration of the reaction mixture, was triturated with $CHCl_3$.

c) A solution of the 3-(2,2,2-trichloroethyloxycarbonyl)benzoyl derivative (1.0 g, 1.6 mmol) in acetic acid (50 mL) was treated with zinc dust (1.0 g, 16 mmol). The mixture was warmed in an oil bath at 50° for 18 hr. While still warm, the mixture was filtered (washing with acetic acid) and, after cooling to room temperature, the filtrate was poured into $H_2O$ (250 mL). The precipitated yellow solid, 6-chloro-5-fluoro-2,3-dihydro-3-[3-carboxybenzoyloxy-(2-thienyl)methylene]-2-oxo-1H-indole-1-carboxamide was collected by filtration and recrystallized from acetic acid: mp 244°–248°. The yield was 130 mg. Anal. calculated for $C_{19}H_{14}ClFN_2O_6S$: C, 50.40; H, 3.12; N, 6.19. Found: C, 51.21; H, 2.96; N, 5.99.

EXAMPLE 14

6-Chloro-5-fluoro-2,3-dihydro-3-[butyloxycarbonyl)-propenoyloxy-(2-thienyl)methylene]-2-oxo-1H-indole-1-carboxamide a) 3-(Butyloxycarbonyl)propenoyl chloride was prepared according to the procedure of Lutz (J. Am. Chem. Soc., 1930, 52, 3430).

b) The title compound was prepared by the procedure of Example 1 with the exception that 3-(butyloxycarbonyl)propenoyl chloride (2 equiv.) and diisopropylethylamine were used. The crude product was purified by flash chromatography (using $CH_2Cl_2$, 95:5 $CH_2Cl_2$/MeOH and then 90:10 $CH_2Cl_2$/MeOH as eluants) followed by recrystallization from acetonitrile: mp 196°–197°. The $^1H$ NMR spectrum indicated the sample to contain only the E geometrical isomer of the title compound. Anal. calculated for $C_{22}H_{18}ClFN_2O_6S$: C, 53.61; H, 3.68; N, 5.68. Found: C, 53.53; H, 3.55; N, 5.78.

EXAMPLE 15

6-Chloro-5-fluoro-2,3-dihydro-3-[3-(octyloxycarbonyl)propenoyloxy-(2-thienyl)methylene]-2-oxo-1H-indole-1-carboxamide a) 3-(Octyloxycarbonyl)propenoyl chloride was prepared according to the procedure of Lutz (J. Am. Chem. Soc., 1930, 52, 3430).

b) The title compound was prepared by the procedure of Example 1 with the exception that 3-(octyloxycarbonyl)propenoyl chloride (2 equiv.) and diisopropylethylamine were used. The crude product was purified by flash chromatography (using 99:1 $CH_2Cl_2$/MeOH as eluant) followed by recrystallization from acetonitrile: mp 140°–148°. The $^1H$ NMR spectrum indicated the sample contained both the E and Z geometrical isomers of the title compound in a ratio of 33:67. Anal. calculated for $C_{26}H_{26}ClFN_2O_6S$: C, 56.88; H, 4.77; N, 5.10. Found: C, 56.81; H, 4.62; N, 5.07.

EXAMPLE 16

6-Chloro-5-fluoro-2,3-dihydro-3-[3-(4-phenylbutyloxycarbonyl)propenoyloxy-(2-thienyl)methylene]-2-oxo-1H-indole-1-carboxamide a) 3-(4-Phenylbutyloxycarbonyl)propenoyl chloride was prepared according to the procedure of Lutz (J. Am. Chem. Soc., 1930, 52, 3430).

b) The title compound was prepared by the procedure of Example 1 with the exception that 3-(4-phenylbutyloxycarbonyl)propenoyl chloride (2 equiv.) and diisopropylethylamine were used. The crude product was purified by flash chromatography (using 98:2 $CH_2Cl_2$/MeOH as eluant) followed by recrystallization from acetonitrile: mp 159°–161°. The $^1H$ NMR spectrum indicated the sample contained both the E and Z geometrical isomers of the title compound in a ration of 27:73. Anal. calculated for $C_{28}H_{22}ClFN_2O_6S$: C, 59.10; H, 3.90; N, 4.92. Found: C, 58.89; H, 3.71; N, 4.72.

EXAMPLE 17

6-Chloro-5-fluoro-2,3-dihydro-3-[octanoyloxy-(2-thienyl)methylene]-2-oxo-1H-indole-1-carboxamide The title compound was prepared by the procedure of Example 1 with the exception that octanoyl chloride (2 equiv.) was used and diisopropylethylamine was the base. The crude product was purified by flash chromatography on silica gel (eluting with $CH_2Cl_2$) followed by recrystallization from acetonitrile: mp 149°–150°. The $^1H$ NMR spectrum indicated the sample contained only the Z geometrical isomer of the title compound. Anal calcd for $C_{22}H_{22}ClFN_2O_4S$: C, 56.83; H, 4.77; N, 6.03. Found: C, 56.85; H, 4.49; N, 6.03.

EXAMPLE 18

6-Chloro-5-fluoro-2,3-dihydro-3-[3-(1-methylpropyloxycarbonyl)propenoyloxy-2-thienyl)methylene]-2-oxo-1H-indole-1-carboxamide a) 3-(1-Methylpropyloxycarbonyl)propenoyl chloride was prepared according to the procedure of Lutz (J. Am. Chem. Soc., 1930, 52, 3430).

b) The title compound was prepared by the procedure of Example 1 with the exception that 3-(1-methylpropyloxycarbonyl)propenoyl chloride (1.2 equiv.) and diisopropylethylamine were used. The crude product was purified by flash chromatography (eluting with $CH_2Cl_2$) followed by recrystallization from acetonitrile: mp 180°–186°. The $^1H$ NMR spectrum indicated the sample contained both the E and Z geometrical isomers of the title compound in a ratio of 60:40. Anal. calcd for $C_{22}H_{18}ClFN_2O_6S$: C, 53.61; H, 3.68; N, 5.68. Found: C, 53.60; H, 3.57; N, 5.67.

EXAMPLE 19

6-Chloro-5-fluoro-2,3-dihydro-3-[3-(methyloxycarbonyl)propanoyloxy-(2-thienyl)methylene]-2-oxo-1H-indole-1-carboxamide The title compound was prepared by the procedure of Example 1 with the exception that 3-(methyloxycarbonyl)propanoyl chloride (2 equiv.) and diisopropylethylamine were used. The crude product was purified by flash chromatography (eluting with 96:4 $CH_2Cl_2$/MeOH) followed by recrystallization from toluene: mp 179°–183°. The $^1H$ NMR spectrum indicated the sample contained both the E and Z geometrical isomers of the title compound in a ratio of 31:69. Anal. calcd for $C_{22}H_{12}ClFN_2O_6S$: C, 54.27; H, 2.48; N, 5.75. Found: C, 53.80; H, 2.18; N, 5.71.

EXAMPLE 20

6-Chloro-5-fluoro-2,3-dihydro-3-[3-(ethyloxycarbonyl)-propanoyloxy-(2-thienyl)methylene]-2-oxo-1H-indole-1-carboxamide The title compound was prepared by the procedure of Example 1 with the exception that 3-(ethyloxycarbonyl)propanoyl chloride (2 equiv.) and diisopropylethylamine (2.2 equiv.) were used. The crude product was purified by flash chromatography (eluting with 97.5:2.5 $CH_2Cl_2$/MeOH) followed by trituration with $CH_2Cl_2$ and recrystallization from acetonitrile: m; 182°–183°. The $^1H$ NMR spectrum indicated the sample contained only the E geometrical isomer of the title compound. Anal. calcd for $C_{20}H_{16}ClFN_2O_6S$: C, 51.45; H, 3.45; N, 6.00. Found: C, 51.38; H, 3.27; N, 5.97.

EXAMPLE 21

6-Chloro-5-fluoro-2,3-dihydro-3-[3-(N,N-diethylcarboxamidomethyl)oxycarbonyl]propanoyloxy-(2-thienyl)methylene]-2-oxo-1H-indole-1-carboxamide a) A solution of succinic anhydride (16.0 g, 160 mmol) and benzyl alcohol (17.1 g, 158 mmol) in toluene (200 mL) was heated at reflux for 3.5 hr. At this time, the solvent was removed in vacuo to leave 3-(benzyloxycarbonyl)propanoic acid as a white solid.

b) A solution of 3-(benzyloxycarbonyl)propanoic acid (15.0 g, 72 mmol), 2-chloro-N,N-diethylacetamide (11.9 g, 79.5 mmol), triethylamine (11.2 mL, 80.4 mmol) and sodium iodide (1.1 g, 7.4 mmol) in ethyl acetate (280 mL) was heated at reflux for 3 hr. The resulting mixture was filtered to remove triethylamine hydrochloride which was washed with more ethyl acetate. The filtrate was washed with 1N HCl solution, saturated $NaHCO_3$ solution and brine. After drying and filtering, the solvent was removed in vacuo to leave benzyl 3-[(N,N-diethylcarboxamidomethyl)oxycarbonyl]propanoate as a vixcous oil (22.2 g).

c) To a solution of benzyl 3-[(N,N-diethylcarboxamidomethyl)oxycarbonyl]propanoate (22.2 g, 62.9 mmol) in ethanol (250 mL) was added 10% palladium on carbon (1.0 g). The mixture was shaken under an atmosphere of hydrogen (3 atmospheres pressure) at 25° for 18 hr. After removal of the catalyst by filtration through diatomaceous earth, the solvent was evaporated to leave 3-[(N,N-diethylcarboxamidomethyl)oxycarbonyl]propanoic acid as a white solid (10.47 g).

d) A solution of 3-[(N,N-diethylcarboxamidomethyl)oxycarbonyl]propanoic acid (5.0 g, 21.6 mmol) and oxalyl chloride (2.0 mL, 23.5 mmol) in benzene (100 mL) was heated at reflux for 1 hr. The solvent was removed in vacuo to leave 3-[(N,N-diethylcarboxamidomethyl)oxycarbonyl]propanoyl chloride as an oil.

e) The title compound was prepared by the procedure of Example 1 with the exception that 3-[(N,N-diethylcarboxamidomethyl)oxycarbonyl]propanoyl chloride (2.2 equiv.) and diisopropylethylamine (2.2 equiv.) were used. The crude product was purified by flash chromatography (eluting with $CH_2Cl_2$ and then 97.5:2.5 $CH_2Cl_2$/MeOH) followed by trituration with 1:1 ether/$CH_2Cl_2$ and recrystallization from toluene: mp 165°–167°. The $^1H$ NMR spectrum indicated the sample contained only the E geometrical isomer of the title compound. Anal. calcd for $C_{24}H_{23}ClFN_3O_7S$: C, 52.22; H, 4.20; N, 7.61. Found: C, 52.17; H, 4.06; N, 7.50.

EXAMPLE 22

5-Chloro-2,3-dihydro-3-[3-carboxypropenoyloxy-(2-thienyl)methylene]-2-oxo-1H-indole-1-carboxamide a) 3-(2-Trimethylsilylethyloxycarbonyl)propenoyl chloride was prepared according to a modification of the procedure of Lutz (J. Am. Chem. Soc., 1930, 52, 3430) in which remaining fumaryl chloride and unwanted diester are removed by distillation under vacuum leaving the desired acid chloride behind in the pot.

b) The title compound was prepared by the procedure of Example 1 with the exception the 3-(2-trimethylsilylethyloxycarbonyl)propenoyl chloride (1.3 equiv.), 5-chloro-2,3-dihydro-3-[hydroxy-(2-thienyl)-methylene]-2-oxo-1H-indole-1-carboxamide and diisopropylethylamine were used. The crude product was purified by flash chromatography (using 98:2 $CH_2Cl_2$/EtOAc as eluant) followed by recrystallization from acetonitrile.

c) Hydrogen fluoride/pyridine complex (20 mL) was cooled in an ice bath in a polyethylene bottle. The 3-(2-trimethylsilylethyloxycarbonyl)propenoyl derivative (0.89 g, 1.71 mmol) was then added. The resulting slurry was agitated in the cold for 0.5 hr. The reaction was then quenched by addition of $H_2O$. The product was collected by filtration, washing with $H_2O$ and dried in vacuo. The yield was 0.60 g, mp 198°–200°. The $^1H$ NMR spectrum indicated the sample contained only the E geometrical isomer of the title compound. Anal. calcd for $C_{18}H_{11}ClN_2O_6S$: C, 51.62; H, 2.65; N, 6.69. Found: C, 51.18; H, 2.62; N, 6.51.

EXAMPLE 23

6-Chloro-5-fluoro-2,3-dihydro-3-[3-carboxpropenoyloxy-(4-chloro-2-thienyl)methylene]-2-oxo-1H-indole-1-carboxamide a) 3-(2-Trimethylsilylethyloxycarbonyl)propenoyl chloride was prepared according to a modification of the procedure of Lutz (J. Am. Chem. Soc., 1930, 52, 3430) in which remaining fumaryl chloride and unwanted diester are removed by distillation under vacuum leaving the desired acid chloride behind in the pot.

b) The title compound was prepared by the procedure of Example 1 with the exception that 3-(2-trimethylsilylethyloxycarbonyl)propenoyl chloride (1.3 equiv.), 6-chloro-5-fluoro-2,3-dihydro-3-[hydroxy-(4-chloro-2-thienyl)methylene]-2-oxo-1H-indole-1-carboxamide and diisopropylethyl-amine were used. The crude product was purified by flash chromatography (using 60:40 hexane/EtOAc as eluant) followed by recrystallization from acetonitrile.

c) Hydrogen fluoride/pyridine complex (20 mL) was cooled in an ice bath in a polyethylene bottle. The 3-(2-trimethylsilylethyloxycarbonyl)propenoyl derivative (0.82 g, 1.43 mmol) was then added. The resulting slurry was agitated in the cold for 0.5 hr. The reaction was then quenched by addition of $H_2O$. The product was collected by filtration, washing with $H_2O$ and dried in vacuo. The yield was 0.50 g, mp 158°. The $^1H$ NMR spectrum indicated the sample contained only the E geometrical isomer of the title compound. Anal. Calcd for $C_{18}H_9Cl_2FN_2O_6S$: C, 45.88; H, 1.92; N, 5.94. Found: C, 45.24; H, 1.98; N, 5.84.

EXAMPLE 24

6-Chloro-5-fluoro-2,3-dihydro-3-[ethoxycarbonylmethoxyacetoxymethoxy-(2-thienyl)methylene]-2-oxo-1H-indole-1-carboxamide a) A solution of diglycolic anhydride (12 g, 0.103 mol) and ethanol (4.74 g, 0.103 mol) in toluene (100 ml) was heated at reflux for 16 hr. The solution was cooled and evaporated and the residue distilled under reduced pressure. The product, monoethyl diglycolate (9.2 g, 55%), was collected over the range 109°–135° C. at 5 torr.

b) Solid $NaHCO_3$ (12.2 g, 0.145 mol) was added, in portions, to a solution of tetrabutylammonium bisulphate (24.6 g, 0.0752 mol) in water (250 ml), followed by a solution of monoethyl diglycolate (11.75 g, 0.0725 mol). The mixture was stirred for 16 hr. and then extracted with methylene chloride (3×500 ml). The combined organic extracts were dried, filtered and evaporated to leave the salt (21.1 g, 72%) which was used without further purification.

c) A solution of the tetrabutylammonium salt of monoethyl diglycolate (16 g, 0.04 mol) in methylene chloride (125 ml) was added to bromochloromethane (200 ml) over 1.5 hr. The resulting solution was stirred at room temperature overnight and then evaporated to dryness. The residue was chromatographed on silica eluting with ethyl acetate/hexane, 40/60 and the fractions containing product combined and evaporated to give ethyl dichloromethyl diglycolate (0.836 g, 10%) as a colorless oil. NMR analysis showed the material to be approximately 70% pure, but was used directly in the next step.

d) The chloromethyl ester (0.836 g, 3.98 mmol) from step c) was dissolved in acetone (10 ml) and then sodium iodide (1.8 g, 11.9 mmol) was added and the mixture stirred for 16 hr. at room temperature. The mixture was filtered and the filtrate evaporated to dryness, redissolved in methylene chloride (25 ml) and then washed with water (10 ml), sodium thiosulphate solution (10 ml), and saturated sodium chloride solution (10 ml). The organic phase was separated, dried and evaporated to give crude ethyl iodomethyl ester diglycolate (1 g) which was used directly in the final step.

e) To a stirred suspension of sodio-6-chloro-5-fluoro-2,3-dihydro-3-[oxy-(2-thienyl)methylene]-2-oxo-1H-indole-1-carboxamide (1.2 g, 3.3 mmol) in acetone (30 ml) was added a solution of the iodomethyl ester from step d) in acetone (10 ml) over 5 minutes. The mixture was stirred for 16 hr. at room temperature. The resulting suspension was diluted with acetone until solution was obtained, silica (2 g) was added and the mixture evaporated to dryness. The resulting dry silica slurry was loaded onto a silica chromatography column and then eluted with ethyl acetate/hexane, 40/60. The fractions containing product were combined and evaporated to give the crude product which was recrystallized from ethanol to afford the title compound as a yellow crystalline solid (136 mg, mp 129°–130° C.).

EXAMPLE 25

6-Chloro-5-fluoro-2,3-dihydro-3-[benzyloxycarbonylmethoxyacetoxymethoxy-(2-thienyl)methylene]-2-oxo-1H-indole-1-carboxamide The title compound was prepared using the same methodology as Example 24 with the exception of using benzyl alcohol instead of ethanol in step a) to give monobenzyl diglycolate which was carried through the remaining procedures. The title compound was a yellow crystalline solid with a mp of 122° C.

EXAMPLE 26

6-Chloro-5-fluoro-2,3-dihydro-3-[1-(benzyloxycarbonylmethoxyacetoxy)ethoxy-(2-thienyl)methylene]-2-oxo-1H-indole-1-carboxamide a) To a solution of monobenzyl diglycolate (7.87 g, 0.035 mmol) in methylene chloride (75 ml) was added thionyl chloride (42 g, 0.35 mol) and the mixture stirred at room temperature for 72 hr. The mixture was evaporated to dryness and the crude acid chloride used directly in the next step.

b) To a mixture of the acid chloride (2.6 g, 0.011 mol) from step a) and a catalytic quantity of fused zinc chloride was added acetaldehyde (0.96 g, 0.022 mol) and the mixture stirred at room temperature for 2 hr. The mixture was then evaporated to dryness and the residue chromatographed on silica, eluting with ethyl acetate/hexane, 30/70. The fractions containing product were combined and evaporated to give a colorless oil (1.1 g, 35%).

c) To a stirred suspension of sodio-6-chloro-5-fluoro-2,3-dihydro-3-[oxy-(2-thienyl)methylene]-2-oxo-1H-indole-1-carboxamide (0.95 g, 2.62 mmol) in acetone (20 ml) was added a solution of the chloroethyl ester from step b) in acetone (10 ml) over 5 minutes. Sodium iodide (0.13 g, 0.87 mmol) was then added and the mixture heated at reflux for 7 hr. The resulting suspension was cooled, diluted with acetone until solution was obtained, silica (2 g) was added and the mixture evaporated to dryness. The resulting dry silica slurry was loaded onto a silica chromatography column and then eluted with ethyl acetate/hexane, 40/60. The fractions containing product were combined and evaporated to give the crude product. Recrystallization from ether afforded the title compound as a yellow crystalline solid (20 mg, mp 89°–91° C.).

EXAMPLE 27

6-Chloro-5-fluoro-2,3-dihydro-3-[benzyloxycarbonyl-methoxyacetoxy-(2-thienyl)methylene]-2-oxo-1H-indole-1-carboxamide To a cooled (0° C.), stirred solution of 6-chloro-5-fluoro-2,3-dihydro-3-[oxy-(2-thienyl)-methylene]-2-oxo-1H-indole-1-carboxamide (1 g, 3 mmol) and triethylamine (0.33 g, 3.3 mmol) in methylene chloride (10 ml) was added a solution of monobenzyl diglycolate acid chloride (0.79 g, 3.3 mmol) (see Example 26, step a) in methylene chloride (10 ml) over 5 minutes. The mixture was stirred at room temperature for 2 hr. and then absorbed on silica and chromatographed, eluting with methylene chloride/methanol, 15/1. Fractions containing product were combined and evaporated, and the crude product recrystallized from acetonitrile to afford the title compound as a yellow crystalline solid (40 mg, mp 189°–190° C.).

EXAMPLE 28

6-Chloro-5-fluoro-2,3-dihydro-3-[N,N-diethylcarbamoylmethoxyacetoxy-(2-thienyl)methylene]-2-oxo-1H-indole-1-carboxamide a) To a stirred solution of diglycolic anhydride (1 g, 8.6 mmol) in toluene (10 ml) was added diethylamine (0.628 g, 8.6 mmol) over 10 min. A mild exotherm resulted and the mixture was allowed to stir at room temperature for 16 hr. Evaporation of the solvent afforded the product as a colorless, viscous oil (1.7 g, 100%).

b) To a solution of N,N-diethylcarbamoylmethoxy acetic acid (1.5 g, 7.3 mmol) in methylene chloride (15 ml) was added thionyl chloride (8.7 g, 73 mmol) and the mixture stirred at room temperature for 16 hr. Evaporation of the solvent furnished the crude acid chloride which was used directly in the next step.

c) To a stirred solution of 6-chloro-5-fluoro-2,3-dihydro-3-[oxy-(2-thienyl)-methylene]-2-oxo-1H-indole-2-carboxamide (2.7 g, 8.2 mmol) and triethylamine (1 g, 9.8 mmol) in methylene chloride (20 ml) was added a solution of N,N-diethylcarbamoylmethoxy acetyl chloride (1.7 g, 8.2 mmol) in methylene chloride (10 ml) over 5 minutes. The mixture was stirred at room temperature for 72 hr. and then absorbed on silica and chromatographed, eluting with methylene chloride/methanol, 25/1. Fractions containing product were combined and evaporated, and the crude product recrystallized from acetone to afford the title compound as a yellow crystalline solid (126 mg, mp 205°–208° C.).

EXAMPLE 29

6-Chloro-5-fluoro-2,3-dihydro-3-[(2-(1,1-dimethylethoxy carbonyamino)propanoyloxy)methoxy-(2-thienyl)methylene]-2-oxo-1H-indole-1-carboxamide The tetrabutylammonium (TBA+) salt of N-t-BOC alanine (50 mmole) (prepared by titration with TBA+ hydroxide in ethanol or by treatment with an equivalent of TBA+ HSO$_4$− and 2 equivalents NaHCO$_3$ in water and extraction with a chlorocarbon) was dissolved in BrCH$_2$Cl (200 ml) and stirred for 48 hr. in the dark. The concentrated mixture was taken up in CHCl$_3$, washed with water, dried with MgSO$_4$, filtered and concentrated to an oil. This was chromatographed (CH$_2$Cl$_2$) to give 6.25 g (52%) of N-t-BOC alanine chloromethyl ester which contained a trace of the corresponding bromomethyl ester.

N-t-BOC Alanine chloromethyl ester (6.20 g, 26.1 mmole) and sodium iodide (19.5 g, 130 mmole) were combined in acetone (150 ml) and stirred at room temperature for 18 hr. The mixture was then filtered and the filtrate concentrated to an oil. This was taken up in EtOAc and washed with 10% sodium thiosulfate solution and water. Drying with MgSO$_4$, filtration and concentration yielded 7.40 g (86%) of N-t-BOC alanine iodomethyl ester as an oil.

N-t-BOC alanine iodomethyl ester (7.30 g, 22.2 mmole) and the sodium salt of 3-[hydroxy-(2-thienyl)-methylene]-6-chloro-5-fluoro-2,3-dihydro-2-oxo-1H-indole-1-carboxamide (2.67 g, 7.4 mmole) were combined in acetone (75 ml) and refluxed for 6 hr. The reaction mixture was concentrated and the residue preabsorbed onto silica gel, charged onto a column and chromatographed (CH$_2$Cl$_2$ to 5:95-CH$_3$OH:CH$_2$Cl$_2$). Combination and concentration of the appropriate fractions gave the crude product which was recrystallized (EtOAc/hexane) to give 1.16 g (29%) of the title compound: mp 165°–170° C.; Anal. calcd for C$_{23}$H$_{23}$ClFN$_3$O$_7$S: C, 51.16; H, 4.29; N, 7.78. Found: C, 51.26; H, 4.10; N, 7.70

Examples 30–40 were prepared by the procedure of Example 29.

The general structure of these compounds is

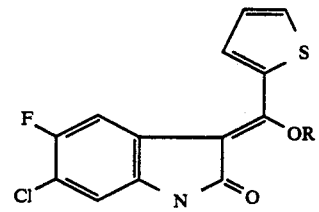

Physical properties and the values of "R" are shown in the Table below.

| Example Number | Starting Acid | mp | Calculated Found | | | R |
|---|---|---|---|---|---|---|
| | | | C | H | N | |
| Example 30 C$_{18}$H$_{14}$ClFN$_2$O$_6$S | O-trimethyl-silylethyl-lactic acid* | 184–187° C. | 49.04 49.19 | 3.20 2.97 | 6.35 6.33 | |

-continued

| Example Number | Starting Acid | mp | Calculated Found C | H | N | R |
|---|---|---|---|---|---|---|
| Example 31 C$_{25}$H$_{20}$ClFN$_2$O$_6$S | O-benzyl lactic acid | 108–112° C. | 56.55 56.44 | 3.80 3.62 | 5.28 5.33 | (structure) |
| Example 32 C$_{22}$H$_{21}$ClFN$_3$O$_5$S | N-t-BOC glycine | 171–174° C. | 50.24 50.40 | 4.02 3.53 | 7.99 7.81 | (structure) |
| Example 33 C$_{20}$H$_{16}$ClFN$_2$O$_6$S | tetrahydro furoic acid | 184–185° C. | 51.45 51.37 | 3.45 3.37 | 6.00 5.96 | (structure) |
| Example 34 C$_{19}$H$_{16}$ClFN$_2$O$_6$S | O-methyl lactic acid | 149–151° C. | 50.17 50.21 | 3.55 3.36 | 6.16 6.17 | (structure) |
| Example 35 C$_{27}$H$_{24}$ClFN$_2$O$_6$S | O-benzyl 2-hydroxy-valeric acid | 121–123° C. | 58.01 57.91 | 4.33 4.00 | 5.01 4.99 | (structure) |
| Example 36 C$_{26}$H$_{22}$ClFN$_2$O$_6$S | O-benzyl butyric acid | 111–113° | 57.30 57.30 | 4.07 3.80 | 5.14 5.15 | (structure) |
| Example 37 C$_{27}$H$_{24}$ClFN$_2$O$_6$S | O-benzyl isovaleric acid | 138–142° C. | 58.01 58.06 | 4.33 4.11 | 5.01 5.02 | (structure) |
| Example 38 C$_{24}$H$_{18}$ClFN$_2$O$_6$S | O-benzyl glycolic acid | 130–131° C. | 55.76 55.85 | 3.51 3.48 | 5.42 5.38 | (structure) |
| Example 39 C$_{18}$H$_{14}$ClFN$_2$O$_6$S | O-methyl glycolic acid | 144–147° C. | 49.04 49.00 | 3.20 3.04 | 6.35 6.25 | (structure) |
| Example 40 C$_{20}$H$_{18}$ClFN$_2$O$_6$S | O-methyl butyric acid | 134–135° C. | 51.23 51.52 | 3.87 3.96 | 5.97 5.83 | (structure) |

*A separate step for removing the SEM group was not necessary as it cleaved during the final step of the reaction sequence.

EXAMPLE 41

General Procedures

N-t-BOC Protected amino acid derivatives of 3-[hydroxy-(2-thienyl)methylene]-6-chloro-5-fluoro-2,3-dihydro-2-oxo-1H-indole-1-carboxamide were converted to the corresponding deprotected compounds by two methods:

Method A: The N-t-BOC protected amino acid derivative was dissolved in chilled (ice-water bath) TFA (0.1M) and allowed to stir at that temperature for 1 hr. One equivalent of p-TsOH•H$_2$O was added to this solution and then the TFA was removed in vacuo. After chasing with toluene (2×) to further remove TFA, the residual solid was recrystallized from CH$_3$OH/EtOAc to give the desired deprotected compound.

Method B: The N-t-BOC protected amino acid derivative was dissolved in 2/1 dioxane/EtOAc (0.1M) and this solution saturated with HCl gas while keeping the temperature below 10° C. After 3 hr. the precipitated product was collected, washed with EtOAc and recrystallized from EtOAc/EtOH to give the desired deprotected compound.

Examples 42-45-5 were prepared by method A or B of Example 41.

chloride (21.48 g, 78.2 mmole). After 30 min., acetaldehyde (3.44 g, 78 mmole) was added at 0° C. The reaction mixture was stirred at room temperature for 30 min. and then diluted with CH$_2$Cl$_2$. The mixture was stirred for another 30 min. and then washed with water (3×). After drying with MgSO$_4$, filtration, and concentration in vacuo, a green/brown solid was obtained that was chromatographed (25:75-CH$_2$Cl$_2$:hexane) to give 7.65 (31%) of 1-chloroethyl 4-(benzyloxycarbonyl)ben-

| Example Number | Method | mp | Calculated Found C | H | N | R |
|---|---|---|---|---|---|---|
| Example 42 C$_{17}$H$_{13}$ClFN$_3$O$_5$S. C$_7$H$_8$O$_3$S GLy | A | 210–211° C. | 48.20 48.19 | 3.51 3.56 | 7.03 6.85 | 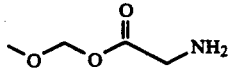 |
| Example 43 C$_{18}$H$_{15}$ClFN$_3$O$_5$S. C$_7$H$_8$O$_3$S L-Ala | A | 210–214° C. | 49.06 48.95 | 3.79 3.67 | 6.87 6.84 | 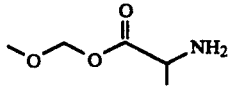 |
| Example 44 C$_{24}$H$_{19}$ClFN$_3$O$_5$S. C$_7$H$_8$O$_3$S L-Phe | A | 150° C. dec. | 54.10 53.85 | 3.96 3.97 | 6.11 5.95 | 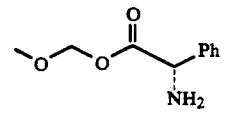 |
| Example 45 C$_{21}$H$_{22}$ClFN$_4$O$_5$S. 2HCl.H$_2$O L-Lys | B | 135° C. dec. | 42.98 42.69 | 4.29 4.62 | 9.55 9.49 | 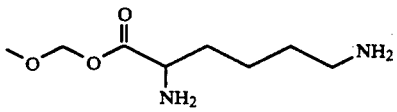 |
| Example 45-1 C$_{20}$H$_{19}$ClFN$_3$O$_5$S. C$_7$H$_8$O$_3$S L-Val | A | 168–173° C. | 50.66 50.44 | 4.25 4.36 | 6.56 6.24 | 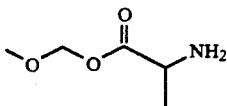 |
| Example 45-2 C$_{21}$H$_{21}$ClFN$_3$O$_5$S. C$_7$H$_8$O$_3$S L-Leu | A | 210–211° C. | 51.41 51.52 | 4.47 4.73 | 6.42 6.04 | 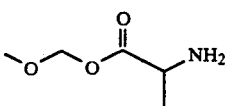 |
| Example 45-3 C$_{19}$H$_{15}$ClFN$_3$O$_7$S. HCl.0.4C$_4$H$_8$O$_2$ L-Asp | B | 105dcc | 44.94 44.50 | 3.54 3.91 | 7.25 6.86 | 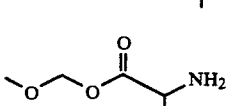 |
| Example 45-4 C$_{20}$H$_{19}$ClFN$_3$O$_5$S$_2$. C$_7$H$_8$O$_3$S L-Met | A | 190–196° | 48.24 48.15 | 4.05 3.90 | 6.25 5.85 | 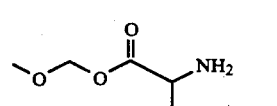 |
| Example 45-5 C$_{18}$H$_{15}$ClFN$_3$O$_5$S. C$_7$H$_8$O$_3$S D-Ala | A | 202–205 dcc | 49.06 48.82 | 3.79 3.58 | 6.87 6.79 | 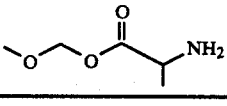 |

EXAMPLE 46

6-Chloro-5-fluoro-2,3-dihydro-3-yl)[(1-(4-phenylmethoxycarbonylbenzoyloxy)-1-ethyloxy-(2-thienyl)methylene]-2-oxo-1H-indole-1-carboxamide Zinc chloride (524 mg) was fused in vacuo and, after cooling, treated with 4-(benzyloxycarbonyl)benzoyl zoate as a white solid: mp 79°-82° C.; Anal. calcd for C$_{17}$H$_{15}$ClO$_4$; C, 64.06; H, 4.74. Found: C, 63.88; H, 4.44. This chloroethyl ester (4.00 g, 12.5 mmole) was combined with the sodium salt of 3-[hydroxy-(2-thienyl)methylene]-6-chloro-5-fluoro-2,3-dihydro-2- oxo-1H-indole-1-carboxamide (4.51 g, 12.5 mmole) and sodium iodide (644 mg, 4.3 mmole) in acetone (40 ml) and refluxed for 12 hr. The reaction mixture was filtered and the filtrate concentrated in vacuo. The orange/brown gum was chromatographed (25:75-EtOAc: hexane, then 1:99-EtOAc:CH$_2$Cl$_2$) to give 1.947 g (25%) of an orange foam: Anal. calcd. for C$_{31}$H$_{22}$ClFN$_2$O$_7$S•2/3H$_2$O: C, 58.81; H, 3.72; N, 4.43. Found: C, 58.74; H, 3.38; N, 4.38.

Example 47 was prepared by the same sequence of reactions:

| Example Number | Starting Acid Chloride | mp | Calculated Found C | H | N | R |
|---|---|---|---|---|---|---|
| Example 47 C$_{31}$H$_{22}$ClFN$_2$O$_7$S | 3-(benzyloxy-carbonyl)-benzoyll chloride | 185-188° C. | 55.95 59.79 | 3.57 3.46 | 4.51 4.45 | 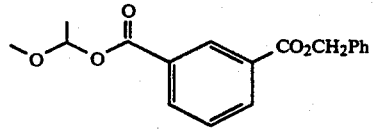 |

EXAMPLE 49

3-[[[(5-benzyloxy)glutaryl]methylene]oxy-(2-thienyl)-methylene]-6-chloro-5-fluoro-2,3-dihydro-2-oxo-1H-indole-1-carboxamide A mixture of 114 g (0.24 mol) of tetrabutylammonium benzylglutarate (A. R. English, D. Girard, V. J. Jasys, R. J. Martingano, and M. S. Kellogg, J. Med. Chem., 1990, 33, 344), and 600 ml of bromochloromethane was stirred at 0° C. in an ice bath with slow warming to room temperature over 16 hr. The excess bromochloromethane was removed in vacuo and the residue was dissolved in EtOAc, washed successively with aqueous 1N hydrochloric acid solution (2s 1L) and satd. aqueous sodium bicarbonate solution (1×2L), dried over sodium sulfate, and evaporated to 35 g of an oil. A mixture of the oil, 55.2 g (0.368 mol) of sodium iodide, and 150 ml of acetone was stirred overnight at room temperature. The residue was partitioned between EtOAc (500 ml) and water (500 ml). The organic layer was separated, washed with satd. aqueous sodium thiosulfate solution (2×500 ml), dried over sodium sulfate, and evaporated to give 34.7 g of a yellow oil which was purified by flash chromatography with an EtOAc-hexane (4:6) eluant to provide 10.7 g (32%) of [[5-(benzyloxy)glutaryl]oxy]methyl iodide as an oil (R$_f$ 0.55, EtOAc-hexane (1:1)). $^1$H NMR (CDCl$_3$) ∂1.92–2.20 (2H, m), 2.41 (2H, t, J=7), 2.45 (2H, t, J=7), 5.16 (s, 2H), 5.88 (2H, s), 7.30–7.40 (5H, m).

A mixture of 20.0 g (0.059 mol) of 3-[hydroxy-(2-thienyl)methyl]-6-chloro-5-fluoro-2,3-dihydro-2-oxo-1H-indole-1-carboxamide, 590 ml (0.059 mol) of aqueous 1N sodium hydroxide solution, and 300 ml of methanol was concentrated in vacuo. The residue was washed well with ether to provide 20.5 g (95%) of the orange-yellow sodium salt.

A suspension of 10.1 g (0.028 mol) of the salt above, 10.0 g (0.028 mol) of [[5-(benzyloxy)glutaryl]oxy]-methyl iodide, and 300 ml of the acetone was stirred for 16 hr. at room temperature. The mixture became homogeneous and was concentrated in vacuo, and the residue was partitioned between 350 ml of EtOAc and 350 ml of satd. aqueous sodium thiosulfate solution. The organic layer was separated, washed again with 350 ml of satd. aqueous sodium thiosulfate solution, dried over sodium sulfate, and concentrated in vacuo. Purification of the 15.6 g of the residual yellow solid by flash chromatography with an EtOAc-hexane (3:7) eluant provided 1.8 g (11%) of the title compound as a yellow solid (R$_f$ 0.3, EtOAc-hexane (1:1). $^1$H NMR (CDCl$_3$) ∂1.90–2.06 (2H, m), 2.32–2.56 (4H, m), 5.12 (2H, s), 5.54 (1H, bd s), 5.72 (2H, s), 7.24–7.27 (1H, m), 7.28–7.41 (5H, m), 7.50–7.53 (1H, m), 7.75–7.78 (2H, m), 8.37–8.41 (2H, m).

EXAMPLE 50

6-Chloro-5-fluoro-3-[[(glutaryl)methylene]oxy-(2-thienyl)methylene]-6-chloro-5-fluoro-2,3-dihydro-2-oxo-1H-indole-1-carboxamide A solution of 1.75 g of 3-[[(5-benzyloxy)glutaryl]methylene]oxy-(2-thienyl)methylene]-6-chloro-5-fluoro-2,3-dihydro-2-oxo-1H-indole-1-carboxamide in 200 ml of EtOAc was hydrogenated at 45 psi in the presence of 900 mg Pd(OH)$_2$ for 2.5 hr. An additional 900 mg of catalyst was added followed by another 900 mg several hours later. Hydrogenation then was continued overnight. The catalyst was filtered and the filtrate was concentrated in vacuo to 2.2 g of an orange semi-solid. Purification by flash chromatography with a methanol-chloroform (2-98 to 10-90) eluant was performed, and the fractions containing the material with R$_f$ 0.3 (methanol-chloroform, 1:9) were pooled and concentrated. The residue was triturated with ether to provide 66 mg (4%) of the title compound as a yellow solid, mp 184°–186° C. $^1$H NMR (DMSO-d$_6$) ∂1.62–1.80 (2H, m), 2.20 (2H, t, J=7), 2.40 (2H, t, J=7), 5.75 (2H, s), 7.30 (1H, t, J=3), 7.65 (1H, d, J=2), 7.76–7.85 (2H, m), 7.95 (1H, s), 8.05 (1H, d, J=3), 8.25 (1H, d, J=7), 8.32 (1H, s). MS (m/e) 337 and 339, 295 and 297, 211 and 213 (base).

EXAMPLE 51

6-Chloro-5-fluoro-2,3-dihydro-3-[(2-furoyl)oxy-(2-thienyl)methylene]-2-oxo-1H-indole-1-carboxamide To a stirred suspension of (Z)- 6-chloro-5-fluoro-2,3-dihydro-3-(hydroxy-2-thienylmethylene)-2-oxo-1H-indole-1-carboxamide sodium salt (1.4 gm., 3.88 mmole) and sodium iodide (20 mg, 0.12 mmole) in 30 ml of dichloromethane was added 2-furoyl chloride (380 mg, 3.88 mmole). The resulting suspension was then stirred for 20 hr. at room temperature. The reaction suspension was filtered and washed with dichloromethane to remove unreacted 6-chloro-5-fluoro-2,3-dihydro-3-(hydroxy-2-thienylmethylene)-2-oxo-1H indole-1-carboxamide sodium salt. The filtrate was evaporated in vacuo to an orange solid which was chromatographed on a silica gel column (100 gm. silica gel) and eluted with dichloromethane to yield the crude titled compound as a solid. The solid was crystallized from dichloromethane and hexane to yield a yellow solid, 210 mg (12.6%): mp 215°–216° C. Anal. calcd. for C$_{19}$H$_{10}$ClFN$_2$O$_5$S: C, 52.73; H, 2.33; N, 6.47. Found: C, 52.66; H, 2.21; N, 6.46.

EXAMPLE 52

6-Chloro-5-fluoro-2,3-dihydro-3-[(acetoxyacetoyl)oxy-(2-thienyl)methylene]-2-oxo-1 H-indole-2-carboxamide To a stirred suspension of (Z)-6-chloro-5-fluoro-2,3-dihydro-3-(hydroxy-2-thienylmethylene)-2-oxo-1H indole-1-carboxamide sodium salt (2.0 gm., 5.6 mmole) and sodium iodide (200 mg, 1.33 mmole) in 25 ml of acetone was added acetoxyacetyl chloride (770 mg, 5.6 mmole) and the mixture was heated to reflux for 18 hr. The suspension was cooled to room temperature and filtered to remove unreacted 6-chloro-5-fluoro-2,3-dihydro-3-(hydroxymethylene)-2-oxo-1H indole-2-carboxamide sodium salt. The filtrate was evaporated in vacuo to a yellow solid which was chromatographed on a silica gel column (silica gel, 75 gm) and eluted with hexane and ethyl acetate (9:1) to yield the crude titled compound as a solid, which was crystallized from acetonitrile to yield a yellow solid, 500 mg (20%): mp 188°–189° C. Anal. calcd. for $C_{18}H_{12}ClFN_2O_6S$: C, 49.27; H, 2.76; N, 6.38. Found: C, 49.14; H, 2.54; N, 6.17.

EXAMPLE 53

6-Chloro-5-fluoro-2,3-dihydro-3-[(methoxyacetoyl)oxy-(2-thienyl)methylene]-2-oxo-1 H-indole-1-carboxamide The title compound was prepared using methoxyacetyl chloride using the procedure described in Example 52 with the exception that the crude product was purified by chromatography (florasil) and eluted with ethyl acetate. Crystallization from acetonitrile gave a yellow solid, 550 mg (24.2%): mp 199°–200.5° C. Anal. calcd. for $C_{17}H_{12}ClFN_2O_5S$: C, 49.70; H, 2.94; N, 6.82. Found: C, 49.51, H, 2.66; n, 6.92.

EXAMPLE 54

6-Chloro-5-fluoro-2,3-dihydro-3-[trans-(2-trimethylsilylethyloxycarbonyl)-2-(cyclobutanoyl)oxy-(2-thienyl)methylene]-2-oxo-1 H-indole-1-carboxamide To a stirred solution of 6-chloro-5-fluoro-2,3-dihydro-3-(hydroxy-2-thienylmethylene)-2-oxo-1H-indole-1-carboxamide (14.1 gm, 0.0416 mmole) in 120 ml of dichloromethane and diisopropylethylamine (6.89 gm, 0.053 mole) was added trans-1-(2-trimethylsilylethyloxycarbonyl)2-cyclobutylcarbonyl chloride (14.0 gm, 0.053 mole). After stirring for 18 hr. at room temperature and filtering the solid that formed, the filtrate was evaporated in vacuo to a yellow solid. The solid was chromatographed on a silica gel column and eluted with hexane and ethyl acetate (3:1) to yield a crude solid, crystallization from acetone gave a yellow solid 1.0 g (4.3%): mp 183°–184° C. Anal. calcd. for $C_{25}H_{26}ClFN_2O_6Si$: C, 53.14; H, 4.64; N, 4.96; Found: C, 53.08; H, 4.45; N, 4.86.

EXAMPLE 55

6-Chloro-5-fluoro-2,3-dihydro-3-[trans-1(2-trimethylsilylethyloxycarbonyl)-2-(cyclopropanoyl)oxy-(2-thienyl)methylene]2-oxo-1H-indole-1-carboxamide Z isomer The title compound was prepared using appropriate starting materials by the procedure of Example 54, with the exception that it was separated on a silica gel pad and eluted with hexane and ethyl acetate (4:1) to give the crude product. Crystallization from chloroform and hexanes gave a yellow solid, 140 mg (3.7%); mp 181°–182° C. Anal. Calcd. for $C_{24}H_{24}ClFN_2O_6SSi$: C, 52.31; H, 4.39; N, 5.08. Found: C, 52.32; H, 4.36; N, 5.12.

EXAMPLE 56

6-Chloro-5-fluoro-2,3-dihydro-3-[trans-1-(2-trimethylsilylethyloxycarbonyl)-2-(cyclopropanoyl)oxy-2-thienyl)methylene]-2-oxo-1H-indole-1-carboxamine E isomer The title compound was prepared using appropriate starting materials by the procedure of Example 54. Crystallization from chloroform and hexanes gave a yellow solid, 160 mg (4.2%); mp 175–176. Anal. calcd. for $C_{24}H_{24}ClFN_2O_6SSi$: C, 52.31; H, 4.39; N, 5.08. Found: C, 52.45; H, 4.28; N, 4.92.

EXAMPLE 57

6-Chloro-5-fluoro-2,3-dihydro-3[(cyclopentanoyl)oxy-(2-thienyl)methylene]-2-oxo-1H-indole-1-carboxamide The title compound was prepared using appropriate starting materials by the procedure of Example 54, with the exception of the elution of the silica gel chromatography with hexanes and ethyl acetate (7:3) to give a crude solid. Crystallization from acetone and hexanes gave a yellow solid, 260 mg (3.3%): mp 194° C. dec. Anal. calcd. for $C_{20}H_{16}ClFN_2O_4S$: C, 55.24; H, 3.71; N, 6.44. Found: C, 55.31; H, 3.47; N, 6.37.

EXAMPLE 58

6-Chloro-5-fluoro-2,3-dihydro-3[(2,2,3,3-tetramethylcyclopropanoyl)oxy-(2-thienyl)methylene]-2-oxo-1H-indole-1-carboxamide The title compound was prepared using appropriate starting materials by the procedure of Example 54 with the exception of purification by silica gel pad and elution with hexane and ethyl acetate (7:3) to give a crude solid. Crystallization from acetone gave a yellow solid 230 mg (2.5%): mp 202°. Anal. calcd. for $C_{22}H_{20}ClFN_2O_4S$: C, 57.08; H, 4.35; N, 6.05. Found: C, 57.02; H, 4.36; N, 5.87.

EXAMPLE 59

{1-[(1-Carbamoyl-6-chloro-5-fluoro-2-oxo-1,2-dihydroindol-3-ylidene)-thiophen-2-yl-methoxy]-ethoxycarbonyloxy}-acetic acid methyl ester The tetrabutylammonium salt of 3-[hydroxy-(2-thienyl)methylene]-6-chloro-5-fluoro-2,3-dihydro-2-oxo-1H-indole-1-carboxamide (2.98 g) and methyl (1-iodoethoxy)carbonyloxyacetate (2.18 g) were combined in acetone, and the solution stirred for 20 hr. at 20° C. Solvent was evaporated in vacuo, and the residue extracted with ethyl ether. The ether solution was evaporated in vacuo, to leave a partially crystallized residual oil upon standing. After filtering off the remaining oil, residual solids were slurried in a small amount of ethyl ether and filtered to give 495 mg of yellow solid. An additional 295 mg of comparable quality title product was obtained by chromatography on silica gel (elution with chloroform with 2% acetone) of the combined ether soluble residues. The product was identified by NMR. NMR data for Examples 59–70 are shown in the Table following Example 70.

EXAMPLE 60

{1-[(1-Carbamoyl-6-chloro-5-fluoro-2-oxo-1,2-dihydroindol-3-ylidene)-thiophen-2-ylmethoxy]-ethoxycarbonyloxy}-N,N-dimethylacetamide The tetrabutylammonium salt of 3-[hydroxy-(2-thienyl)methylene]-6-chloro-5-fluoro-2,3-dihydro-2-oxo-1H-indole-1-carboxamide (6.25 g) and N,N-dimethyl-(1-iodoethoxy)carbonyloxyacetamide (5.55 g) were combined in 60 mL of acetone, and the solution stirred for 90 hr. at 20° C. The precipitate present was removed by filtration and dried in vacuo. The solids were chromatographed on silica gel, eluting with 90:10 chloroform:acetone. Fractions containing the title product were combined and evaporated. The residue was slurried with a small amount of ethyl ether and filtered to give 820 mg of yellow solid, mp 194.5°-195.5° C.

EXAMPLE 61

{1-[1-Carbamoyl-6-chloro-5-fluoro-2-oxo-1,2-dihydroindol-3-ylidene)-thiophen-2-ylmethoxy]-ethoxycarbonyloxy}-N,N-diethylacetamide The tetrabutylammonium salt of 3-[hydroxy-(2-thienyl)methylene]-6-chloro-5-fluoro-2,3-dihydro-2-oxo-1H-indole-1-carboxamide (13.85 g) and N,N-diethyl-(1-iodoethyoxy)carbonyloxyacetamide (13.6 g) were combined in 100 mL of acetone, and the solution stirred for 42 hr. at 20° C. Insolubles were removed by filtration, and stirred with chloroform. Remaining solids were filtered off, and the chloroform solution evaporated in vacuo. The residue was chromatographed on silica gel, with 90:10 chloroform:acetone elution. Fractions containing the desired material were combined and evaporated. The residue was slurried with a small amount of ethyl ether and filtered to give 2.37 g of yellow solid, mp 172°-174° C.

EXAMPLE 62

{1-[1-Carbamoyl-6-chloro-5-fluoro-2-oxo-1,2-dihydroindol-3-ylidene)-thiophen-2-ylmethoxy]-methyl} ester of N,N-dimethylsuccinamic acid The tetrabutylammonium salt of 3-[hydroxy-(2-thienyl)methylene]-6-chloro-5-fluoro-2,3-dihydro-2-oxo-1H-indole-1-carboxamide (6.65 g) and iodomethyl N,N-dimethylsuccinamate (3.27 g) were combined in 100 mL of acetone, and the solution stirred for 65 hr. at 20° C. After evaporation of the solvent in vacuo, the residue was extracted 3 times with chloroform. The chloroform extracts were combined and evaporated in vacuo. The residue was chromatographed on silica gel eluted with 75:25 chloroform:acetone. Fractions rich in the title product were combined and evaporated to give 189 mg of orange oil. Other fractions containing the title product were combined, evaporated, and re-chromatographed on silica gel with 90:10 chloroform:acetone. Fractions rich in title product were combined with the 189 mg of oil indicated above and evaporated to give 490 mg of an orange solid. This solid was slurried in a small amount of ethyl ether, and filtered to give 180 mg of orange solid melting at 183°-187° C.

EXAMPLE 63

{[(1-Carbamoyl-6-chloro-5-fluoro-2-oxo-1,2-dihydroindol-3-ylidene)-thiophen-2-yl-methoxy]-methyl} ester of N,N-diethylsuccinamic acid The tetrabutylammonium salt of 3-[hydroxy-(2-thienyl)methylene]-6-chloro-5-fluoro-2,3-dihydro-2-oxo-1H-indole-1-carboxamide (4.36 g) and iodomethyl N,N-diethylsuccinamate (2.36 g) were combined in 30 mL of acetone, and the solution stirred for 87 hr. at 20° C. After evaporation of the solvent in vacuo, the residue was chromatographed on silica gel with 90:10 chloroform:acetone elution. Fractions containing the title product were combined and concentrated to an oil containing some solids. Ethyl ether was added to the oily solids, and insolubles filtered off. (The solids contained both TBA iodide and C-alkylated product.) The ether filtrate was evaporated, and the residue chromatographed on silica gel with 90:10 chloroform:acetone elution. Fractions rich in title product were combined and evaporated in vacuo to an orange oil. The oil was dissolved in ethyl ether and allowed to stand overnight. A precipitate of yellow solids was removed by filtration and dried in vacuo to give 265 mg, melting at 151°-152.5° C.

EXAMPLE 64

{[(1-Carbamoyl-6-chloro-5-fluoro-2-oxo-1,2-dihydroindol-3-ylidene)-thiophen-2-ylmethoxy]-methyl} ester of N,N-dipropylsuccinamic acid The tetrabutylammonium salt of 3-[hydroxy-(2-thienyl)methylene]-6-chloro-5-fluoro-2,3-dihydro-2-oxo-1H-indole-1-carboxamide (6.07 g) and iodomethyl N,N-dipropylsuccinamate (2.6 g) were combined in 50 ml of acetone, and the solution stirred for 18 hr. at 20° C. The solvent was evaporated in vacuo, and the residue stirred with ethyl ether. A precipitate formed, and was removed by filtration. The ether solution was evaporated in vacuo to give 6.5 g of orange oil. The oil was chromatographed on silica gel with 95:5 chloroform:acetone elution. Fractions rich in the title product were combined and concentrated in vacuo. Ethyl ether was added to the residue and the solution was allowed to stand. The yellow precipitate which formed was filtered off to give 210 mg..Other fractions that contained the title product were combined and evaporated, and the residue chromatographed on silica gel with 50:50 ethyl acetate:hexane elution. Fractions rich in the title product were combined and concentrated to an oil, which was dissolved in ethyl ether and allowed to stand for 18 hr. The yellow precipitate which formed was filtered off to give an additional 220 mg, mp 131.5°-133.5° C.

EXAMPLE 65

{[(1-Carbamoyl-6-chloro-5-fluoro-2-oxo-1,2-dihydroindol-3-ylidene)-thiophen-2-ylmethoxy]-methyl} ester of N,N-hexamethylenesuccinamic acid The tetrabutylammonium salt of 3-[hydroxy-(2-thienyl)methylene]-6-chloro-5-fluoro-2,3-dihydro-2-oxo-1H-indole-1-carboxamide (4.4 g) and iodomethyl 4-homopiperidino-4-oxobutyrate (11.98 g) were combined in 30 mL of acetone, and the solution stirred for 17 hr. at 20° C. The mixture was filtered, and the filtrate concentrated in vacuo. The residue was chromatographed on silica gel with 93:7 chloroform:acetone elution. Fractions rich in title product were combined and concentrated to an orange oil. This oil was chromatographed on silica gel using the same elution solvent. Fraction rich in the title product were combined and evaporated. Ethyl ether was added to the residue and the solution allowed to stand. The yellow precipitate which formed was removed by filtration to give 250 mg of material, mp 149°–151° C.

EXAMPLE 66

{[(1-Carbamoyl-6-chloro-5-fluoro-2-oxo-1,2-dihydroindol-3-ylidene)-thiophen-2-ylmethoxy]-methyl} ester of N,N-dimethylcarbamoyloxyacetic acid The tetrabutylammonium salt of 3-[hydroxy-(2-thienyl)methylene]-6-chloro-5-fluoro-2,3-dihydro-2-oxo-1H-indole-1-carboxamide (3.28 g) and iodomethyl N,N-dimethylaminocarbonyloxyacetate (1.18 g) were combined in 15 mL of acetone and the solution stirred for 17 hr. at 20° C. The mixture was filtered, and the filtrate concentrated in vacuo. The residue was chromatographed on silica gel with 95:5 chloroform:acetone elution. Fractions rich in title product were combined and concentrated to a yellow oil. Ethyl ether was added to the oil, and the solution allowed to stand. A yellow precipitate formed, was removed by filtration and dried to give 240 mg, mp 185.5°–187° C.

EXAMPLE 67

{[(1-Carbamoyl-6-chloro-5-fluoro-2-oxo-1,2-dihydroindol-3-ylidene)-thiophen-2-ylmethoxy]-methyl} ester of N,N-diethylcarbamoyloxyacetic acid The tetrabutylammonium salt of 3-[hydroxy-(2-thienyl)methylene]-6-chloro-5-fluoro-2,3-dihydro-2-oxo-1H-indole-1-carboxamide (11.66 g) and iodomethyl N,N-diethylaminocarbonyloxyacetate (6.36 g) were combined in 100 mL of acetone, and the mixture stirred for 17 hr. at 20° C. After filtration, the filtrate was concentrated in vacuo to a semi-solid. Ethyl ether was added, and the ether insolubles filtered off. The ether solution was allowed to stand for several hours. The white precipitate which formed was filtered off (C-alkylated product). Upon further standing, the ether filtrate deposited a precipitate of yellow solids. The yellow solid was filtered and dried to give 990 mg of crystals melting at 156.8°–157.8° C.

EXAMPLE 68

{[(1-Carbamoyl-6-chloro-5-fluoro-2-oxo-1,2-dihydroindol-3-ylidene)-thiophen-2-ylmethoxy]-methyl} ester of N-pivaloylglycine The tetrabutylammonium salt of 3-[hydroxy-(2-thienyl)methylene]-6-chloro-5-fluoro-2,3-dihydro-2-oxo-1H-indole-1-carboxamide (2.80 g) and iodomethyl N-pivaloylglycinate (1.45 g) were combined in 20 mL of acetone, and the mixture stirred for 17 hr. at 20° C. After evaporation of the solvent in vacuo, the yellow-orange residue was slurried with ethyl ether and filtered. The ether filtrate was evaporated, and the residue stirred with a small amount of ethyl ether. An insoluble precipitate was removed by filtration, and dissolved in ethyl acetate for chromatography on silica gel with ethyl acetate elution. Fractions containing the title product were combined, and evaporated to a yellow solid. This solid was slurried in a small amount of ethyl ether and filtered to give 140 mg, mp 200°–204° C.

EXAMPLE 69

{[(1-Carbamoyl-6-chloro-5-fluoro-2-oxo-1,2-dihydroindol-3-ylidene)-thiophen-2-ylmethoxy]-methyl} ester of N-(2-ethylbutyryl)glycine The tetrabutylammonium salt of 3-[hydroxy-(2-thienyl)methylene]-6-chloro-5-fluoro-2,3-dihydro-2-oxo-1H-indole-1-carboxamide (5.13 g) and iodomethyl N-(2-ethylbutyryl)glycinate (2.78 g) were combined in 35 mL of acetone, and the mixture stirred for 17 hr. at 20° C. After evaporation of the solvent in vacuo, the orange residue was slurried with ethyl ether and filtered. The ether filtrate was evaporated, and the residue stirred with a small amount of ethyl ether. A yellow precipitate (200 mg) was removed by filtration, and dissolved in ethyl acetate for chromatography on silica gel with ethyl acetate elution. Fractions containing the title product were combined, and evaporated to give 40 mg of yellow solid. An additional 256 mg of the same title product was obtained by chromatography of the initial acetone insoluble fraction on silica gel with ethyl acetate elution.

EXAMPLE 70

{1-[(1-Carbamoyl-6-chloro-5-fluoro-2-oxo-1,2-dihydroindol-3-ylidene)-thiophen-2-ylmethoxy]-ethyl} ester of isopropylcarbonic acid The tetrabutylammonium salt of 3-[hydroxy-(2-thienyl)methylene]-6-chloro-5-fluoro-2,3-dihydro-2-oxo-1H-indole-1-carboxamide (13.62 g) and 1-iodoethyl isopropyl carbonate[1] (6.08 g) were combined in 90 mL of acetone, and the mixture stirred for 17 hr. at 20° C. Insolubles were filtered off, slurried in chloroform, and filtered. The chloroform filtrate was combined with the acetone soluble reaction fraction, and solvents evaporated in vacuo. The residue was chromatographed on silica gel with 98:2 chloroform:acetone elution. Fractions containing the title product were combined, and evaporated to give an orange oil. Ethyl ether was added with stirring, and a yellow solid crystallized out. Filtration and drying gave 1.10 g, mp 183°–184° C.

NMR Data for Compounds of Example 59–70

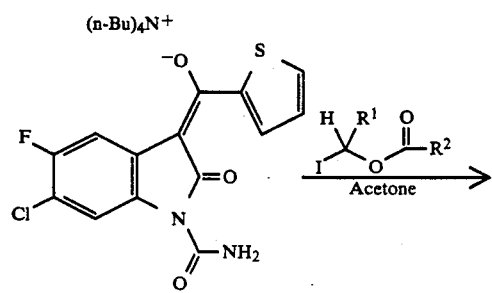

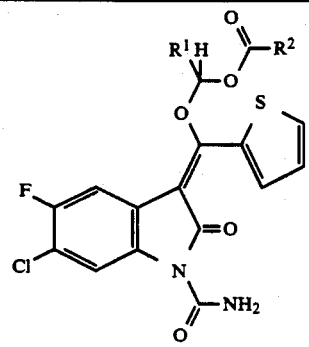

| Example No. | R[1] | R[2] | $^1$H NMR Data (CDCl$_3$) |
|---|---|---|---|
| 59 | Me | OCH$_2$CO$_2$Me | 1.75(d, 3H); 3.68(s, 3H); 4.54(s, 2H); 5.15(br. s, 1H); 6.22(q, 1H); 7.22(dd, 1H); 7.52(dd, 1H); 7.68(dd, 1H); 7.77(d, 1H); 8.36(d, 1H); 8.38(br. s, 1H). |
| 60 | Me | OCH$_2$CONMe$_2$ | 1.75(d, 3H); 2.86(s, 3H); 2.90(s, 3H); 4.62(ABq, 2H); 5.14(br. s, 1H); 6.22(q, 1H); 7.20(dd, 1H); 7.54(dd, 1H); 7.66(dd, 1H); 7.78(d, 1H); 8.34(d, 1H); 8.38(br. s, 1H). |
| 61 | Me | OCH$_2$CONEt$_2$ | 1.11(t, 3H); 2.28(t, 3H); 1.78(d, 3H); 3.16(q, 2H); 3.35(m, 2H); 4.66(ABq, 2H); 5.18(br. s, 1H); 6.26(q, 1H); 7.23(dd, 1H); 7.58(dd, 1H); 7.70(dd, 1H); 7.82(d, 1H); 8.38(d, 1H); 8.42(br. s 1H). |
| 62 | H | CH$_2$CH$_2$CONMe$_2$ | 2.63(m, 4H); 2.90(s, 3H); 3.00(s, 3H); 5.16(br. s, 1H); 5.74(s, 2H); 7.26(dd, 1H); 7.54(dd, 1H); 7.73(dd, 1H); 7.78(d, 1H); 8.40(d, 1H); 8.45(br. s, 1H). |
| 63 | H | CH$_2$CH$_2$CONEt$_2$ | 1.04(t, 3H); 1.16(t, 3H); 2.62(m, 4H); 3.28(m, 4H); 5.22(br. s, 1H); 5.70(s, 2H); 7.22(dd, 1H); 7.50(dd, 1H); 7.69(dd, 1H); 7.74(d, 1H); 8.34(d, 1H); 8.37(br. s, 1H). |
| 64 | H | CH$_2$CH$_2$CONPr$_2$ | 0.80(t, 3H); 0.88(t, 3H); 1.44(m, 2H); 1.56(m, 2H); 2.60(m, 4H); 3.16(q, 4H); 5.15(br. s, 1H); 5.69(s, 2H); 7.20(dd, 1H); 7.46(dd, 1H); 7.68(dd, 1H); 7.74(d, 1H); 8.34(d, 1H); 8.38(br. s, 1H). |
| 65 | H | (CH$_2$)$_2$CON(CH$_2$)$_6$ | 1.44–1.74(m, 8H); 2.60(m, 4H); 3.32–3.46(m, 4H); 5.22(br. s, 1H); 5.70(s, 2H); 7.20(dd, 1H); 7.47(dd, 1H); 7.68(dd, 1H); 7.73(d, 1H); 8.34(d, 1H); 8.36(br. s, 1H). |
| 66 | H | CH$_2$OCONMe$_2$ | 2.86(s, 3H); 2.90(s, 3H); 4.56(s, 2H); 5.14(br. s, 1H); 5.74(s, 2H); 7.20(dd, 1H); 7.45(dd, 1h); 7.58(dd, 1h); 7.72(d, 1H); 8.33(br. s, 1H); 8.34(d, 1H). |
| 67 | H | CH$_2$OCONEt$_2$ | 1.08(t, 3H); 1.11(t, 3H); 3.26(q, 4H); 4.59(s, 2H); 5.24(br. s, 1H); 5.74(s, 2H); 7.20(dd, 1H); 7.44(dd, 1H); 7.68(dd, 1H); 7.72(d, 1H); 8.32(br. s, 1H); 8.32(br. s, 1H); 8.34(d, 1H). |
| 68 | H | CH$_2$NHCOCMe$_3$ | 1.20(s, 9H); 4.04(d, 2H); 5.15(br. s, 1H); 5.75(s, 2H); 6.08(br. s, 1H); 7.27(dd, 1H); 7.50(dd, 1H); 7.75(m, 2H); 8.40(br. s, 1H); 8.42(d, 1H). |
| 69 | H | CH$_2$NHCOCHEt$_2$ | 0.88(t, 6H); 1.43–1.68(m, 4H); 1.05(m, 1H); 4.08(d, 2H); 5.18(br. s, 1H); 5.77(s, 2H); 5.88(br. s, 1H); 7.27(dd, 1H); 7.50(dd, 1H); 7.75(m, 2H); 8.39(br. s, 1H); 8.41(d, 1H). |
| 70 | Me | OCHMe$_2$ | 1.13(d, 3H); 1.35(d, 3H); 1.74(d, 3H); 4.74(m, 1H); 5.20(br. s, 1H); 6.18(q, 1H); 7.24(dd, 1H); 7.56(dd, 1H); 7.72(dd, 1H); 7.80(d, 1h); 8.40(d, 1H); 8.45(br. s, 1H). |

EXAMPLE 71

6-Chloro-5-fluoro-2,3-dihydro-3-[1-(1-(methoxyacetoxy)-ethoxy-(2-thienyl)methylene]oxo-1H-indole-1-carboxamide a) To a mixture of methoxyacetyl chloride (10.0 g, 0.092 mole) and a catalytic quantity of fused zinc chloride was added, cooled the solution to (−20° C.) and added the acetaldehyde (4.06 g, 0.092 mole). Removed cooling and stirred for 1 hr at room temperature. Distilled at 30 torr and collected fractions coming over at 50°–80° C. to yield an oil 3.3 g (22.9%).

To a stirred suspension of sodium-6-chloro-5-fluoro-2,3-dihydro-3-(hydroxy-2-thienylmethylene)-2-oxo-1H-indole-1-carboxamide (3.5 gm, 9.7 mmole) and sodium iodide (500 mg, 3.3 mmole) in 30 ml of acetone was added 1-chloroethylmethoxyacetyl (1.8 gm, 9.7 mmole). The resultant suspension was refluxed for 7 hr, cooled and evaporated in vacuo to yield an orange solid. The solid was chromatographed on a silica gel column (125 ml silica gel) and eluted with hexane and ethyl acetate (9:1) to give the crude product. Crystallization from acetonitrile yielded a yellow solid, 1.1 gm (25%): M.P. 175°–176° C.

Anal. calc'd for $C_{19}H_{16}ClFN_2O_6S$: C, 50.17; H, 3.55; N, 6.16: Found: C, 50.31; H, 3.32; N, 6.32.

EXAMPLE 72

6-Chloro-5-fluoro-2,3-dihydro-3-[1-(morpholinnecarbamoyl)-ethoxy-(2-thienyl)methylene]-2-oxo-1H-indole-1-carboxamide a) To a solution of morpholine (8.7 g, 0.1 mole) and triethylamine (10.1 g, 0.1 mole) in dichloromethane (120 ml) was added 1-chloroethylchloroformate (14.3 g, 0.1 mole) at a rate to keep the solution from refluxing. After stirring for 10 min. the solution was poured into water (200 ml). The organic layer was separated and dried with magnesium sulfate and evaporated to a light brown oil 17.8 g (92%).

To a stirred suspension of sodium-6-chloro-5-fluoro-2,3-dihydro-3-(hydroxy-2-thienylmethylene)-2-oxo-1H-indole-1-carboxamide (10. g, 0.028 mole) and sodium iodide (300 mg, 0.0017 mole) in acetone (45 ml) was added the morpholinecarbamoyl ester from step a) (5.36 g, 0.028 mole) and the mixture refluxed for 5.5 hr. The suspension was cooled and evaporated to a solid, which was chromatographed on a silica gel column (4.5 cm×42 cm) and eluted with hexane and ethyl acetate (7:3) to give the crude product. Crystallization from acetonitrile gave a yellow solid, 2.37 gm (17.3%): M.P 124°–126° C.

Anal. cal'd for $C_{21}H_{19}ClFN_3O_6S$: C, 50.86; H, 3.86; N, 8.47: Found: C, 50.91; H, 3.78; N, 8.54.

EXAMPLE 73

6-Chloro-5-fluoro-2,3-dihydro-3-[1-(amino-cyclopentoyloxymethoxy-(2-thienyl)methylene]-2-oxo-1H-indole-1-carboxamide-methanesulfonic acid salt a) 1-N-t-BOC-amino-1-cyclopentanecarboxylic acid To a solution of 1-amino-1-cyclopentane carboxylic acid (10.0 g, 0.0774 mole) triethylamine (11.75 g, 0.1161 mole), water (45 ml) and 1,4-dioxane (45 ml) was added BOC-ON (20.9 g, 0.085 mole) with stirring for 7 hr at room temperature. The mixture was extracted with ethyl acetate and the ethyl acetate layer was washed with water (50 ml). The aqueous layer was acidified with citric acid to a pH of 3.5 and extracted with ethyl acetate (2×100 ml). The ethyl acetate layer was dried with magnesium sulfate and evaporated to yield the product as an oil, 14 g (79%).

b) 1-N-t-BOC-amino-1-chloromethylcyclopentanoate

To tetrabutylammonium hydrogen sulfate (22.5 g, 0.066 mole) in water (125 ml) was added slowly sodium bicarbonate (11.1 g, 0.132 mole) and stirred for 15 min. Compound a) in chloroform (250 ml) was added and stirred for 3 hrs. The organic layer was separated and dried with magnesium sulfate and evaporated to an oil. To this oil was added bromochloromethane (225 ml) and the solution was stirred overnight at room temperature. The mixture was evaporated to a viscous oil, which was triturated with ether and filtered. The filtrate was evaporated to yield the crude product as an oil 9.2 g (50%).

c) To a stirred suspension of 6-chloro-5-fluoro-2,3-dihydro-3-(hydroxy-2-thienylmethylene)-2-oxo-1H-indole-1-carboxamide sodium salt (2.85 gm, 7.92 mmole) and sodium iodide (285 mg, 1.9 mmole) in 70 ml of acetone was added 1-N-t-BOC-amino-1-chloromethylenecyclopentanoate (2.2 gm, 7.92 mmole). The resultant suspension was refluxed for 7 hr. The reaction suspension was cooled to room temperature and filtered to remove unreacted 6-chloro-5-fluoro-2,3-dihydro-3-(hydroxy-2-thienylmethylene)-2-oxo-1H-indole-1-carboxamide sodium salt. The filtrate was evaporated in vacuo to an orange solid which was chromatographed on a silica gel pad (75 gm) and eluted with hexane and ethyl acetate (7:3) to yield a solid which was crystallized from acetonitrile to yield a yellow solid, 320 mg (7.1%): M.P. 204° C. dec. Anal. calc'd for $C_{26}H_{27}ClFN_3O_7S$: C, 53.84; H, 4.69; N, 7.24. Found: C, 53.83; H, 4.42; N, 7.29 d) A solution of the 1-N-t-BOC-amino-1-cyclopentanoyl derivative from step c) (410 mg, 0.7 mmole), in 10 ml of trifluoroacetic acid was stirred for 20 min at room temperature. The mixture was evaporated in vacuo to yield an oily solid, added 25 ml of dichloromethane and methanesulfonic acid (67.9 mg, 0.7 mmole) and evaporated in vacuo to a yellow solid. The yellow solid was stirred in 25 ml of dichloromethane for 15 min, filtered to yield a yellow solid, 400 mg (99%): M.P. 230° C. dec.

Anal. calc'd for $C_{22}H_{23}ClFN_3O_8S_2$: C, 45.87; H, 4.02; N, 7.30. Found: C, 45.63; H, 3.95; N, 7.19.

EXAMPLE 74

6-Chloro-5-fluoro-2,3-dihydro-3-[acetoxymethoxycarbonylmethoxy-(2-thienyl)methylene]-2-oxo-1H-indole-1-carboxamide a) To a mixture of acetoxyacetyl chloride (20 g, 0.146 mole and a catalytic quantity of fused zinc chloride was added paraformaldehyde (6.2 g, 0.206 mole); and the mixture was heated on a steam bath for 3.5 hr. After cooling the reaction was distilled and fractions collected from 72°–82° C. and 1.2–1.9 torr to yield 3.2 g as an oil (13%).

b) The title product was prepared using the intermediate from Step a) in the same manner as described for Example 73, with the exception of the ratio of the eluant hexane and ethyl acetate (3:1). Crystallization from acetonitrile gave a yellow solid, 900 mg (8.9%): M.P. 176°–177° C.

Anal. calc'd for $C_{19}H_{14}ClFN_2O_7S$: C, 48.68; H, 3.01; N, 5.98. Found: C, 48.60; H, 3.02; N, 6.00.

EXAMPLE 75

6-Chloro-5-fluoro-2,3-dihydro-3-[benzylmethoxy-(2-thienyl)methylene]2-oxo-1H-indole-1-carboxamide a) The chloromethylbenzoate was prepared in the same manner as in Step a), Example 74. The reaction product was distilled at 74°–76° C. at 2.0 torr to yield the crude product as an oil 16.42 g (50%).

b) The title product was prepared using the intermediate from step a) in the same manner as described for Example 73. Crystallization from ethyl acetate gave a yellow solid, 130 mg (5.5%): M.P. 202°–203° C.

Anal. calc'd for $C_{22}H_{14}ClFN_2O_5S$: C, 55.88; H, 2.98; N, 5.92. Found: C, 55.69; H, 2.69; N, 5.86.

EXAMPLE 76

6-Chloro-5-fluoro-2,3-dihydro-3-[1-acetic acid-1-cyclopentylacetoxymethoxy-(2-thienyl)methylene]-2-oxo-1H-indole-1-carboxamide 1-(4-Methoxybenzyloxycarbonylmethyl)-1-cyclopentaneacetic acid.

a) A mixture of 3,3-tetramethyleneglutaric anhydride (10.0 gm, 5.95 mmole), 4-methoxybenzyl alcohol (8.2 gm, 5.95 mmole) and pyridine (4.7 gm, 5.95 mmole) were combined and heated on a steam bath for 1.5 hr. Cooled, acidified with 6N- HCl dropwise and extracted with ether and ethyl acetate 1/1 (3×150 ml), washed the combined organic layers with a saturated solution of sodium bicarbonate (3×150 ml). The aqueous basic layer was acidified with 6N HCl, extracted with ethyl acetate and ether (200 ml) and dried with magnesium sulfate, evaporated in vacuo to yield a crude oil, 11.6 gm (64%).

b) 1-(4-methoxybenzylocycarbonylmethyl)-chloromethyloxycarbnylmethyclcyclo-penatne was prepared as described in Example 73, Step b). Evaporation gave the crude product as an oil 6.5 g (48%), which was used in Step c).

c) The 4-methoxybenzyloxy derivative of the title compound was prepared in the same manner as described in Example 73 (c). Yield, 300 mg (1.6%) as a red viscous oil.

Anal. calc'd for $C_{32}H_{30}ClFN_2O_8S$: C, 58.49; H, 4.60; N, 4.26. Found: C, 58.89; H, 4.32; N, 4.33 d) The 4-methoxybenzyl derivative from Step c), (400 mg, 0.61 mmole), in 15 ml trifluoroacetic acid was stirred for 45 min, evaporated in vacuo to yield a yellow solid. Added 60 ml of dichloromethane and evaporated. The resultant yellow solid was crystallized from methanol to yield the product 600 mg (15%): M.P. 187°–188° C.

Anal. calc'd for $C_{24}H_{22}ClFN_2O_7S$: C, 53.68; H, 4.13; N, 5.22. Found: C, 53.94; N, 4.04; N, 5.02.

EXAMPLE 77

6-Chloro-5-fluoro-2,3-dihydro-3-[L-prolylmethoxy-(2-thienyl)methylene]-2-oxo-1H-indole-1-carboxamide methane sulfonic acid salt a) The chloromethyl ester of N-t-BOC-L-proline was prepared as described in Example 73, Step b). The crude product was isolated as an oil, 35.4 g (83%).

b) The N-t-BOC-L-prolyl derivative was prepared in the same manner as described in Example 73, Step c). Crystallization from ether and hexane gave a yellow solid, 2.65 g (9.36%): M.P. 168°–169° C.

Anal. calc'd for $C_{25}H_{26}ClFN_3O_7S$: C, 52.96; H, 4.62; N, 7.41. Found: C, 52.85; H, 4.46; N, 7.43.

c) The title compound was prepared in the same manner as described in the Example 73, Step d). Crystallization from 2-propanol gave a yellow solid, 333 mg (34%): M.P. 90°–120° C. amorphous solid.

Anal. calc'd for $C_{20}H_{17}ClFN_3O_5SCH_3SO_3H\frac{1}{2}H_2O$: C, 44.52; H, 3.83; N, 7.42. Found: C, 44.35; H, 3.92; N, 7.23.

EXAMPLE 78

6-Chloro-5-fluoro-2,3-dihydro-3-[1-carboxylic acid-3-piperidylcarbonylmethoxy-(2-thienyl)methylene]-2-oxo-1H-indole-1-carboxamide methane sulfonic acid salt a) The preparation of N-t-BOC-piperidine-3-carboxylic acid is as described in Example 73, Step a). Yielded a crude solid 19 g. Crystallization from ethyl acetate gave a white solid, 11.1 g (48%): M.P. 162°–163° C.

b) The 1-N-t-BOC-piperidine-3-chloromethyl ester was prepared in the same manner as described in Example 73, Step b). Evaporation yield a white moist solid 13.5 g (78%) and was used directly in the next step.

c) The 3-chloromethylester-1-N-t-BOC-piperidine was used to prepare the BOC derivative of the title compound in the same manner as described in Example 73. Crystallization from ether and hexane gave a yellow solid, 580 mg (2.5%): M.P. 145°–146° C.

Anal. calc'd for $C_{26}H_{27}ClFN_3O_7S$: C, 53.84; H, 4.69; N, 7.24. Found: C, 53.82; H, 4.57; N, 7.16 d) The title compound was prepared in the same manner as described in Example 73, Step d). Crystallization from acetone gave a yellow solid, 280 mg (68.7%): M.P. 184°–185° C.

Anal. calc'd for $C_{22}H_{23}ClFN_3O_8S_2$: C, 45.87; H, 4.02; N, 7.30. Found: C, 45.75; H, 3.85; N, 7.17. CP-156,011.

EXAMPLE 79

6-Chloro-5-fluoro-2,3-dihydro-3-[1-carboxy-3-ethyl-3-methylpentanoylmethoxy-(2-thienyl)methylene]-2-oxo-1H-indole-1-carboxamide The title compound was prepared in the same manner as Example 76. Crystallization from acetone and hexane gave a yellow solid, 380 mg (27%): M.P. 124°–125° C.

Anal. calc'd for $C_{23}H_{22}ClFN_2O_7S$: C, 52.62; H, 4.22; N, 5.34. Found: C, 52.83; H, 3.99; N, 5.20.

EXAMPLE 80

6-Chloro-5-fluoro-2,3-dihydro-3-[trans-1-carboxy-2-cyclohexylcarbonylmethoxy(2-thienyl)methylene]-2-oxo-1H-indole-1-carboxamide The title compound was prepared in the same manner as Example 76. Crystallization from acetone gave a yellow solid, 590 mg (28.3%): M.P. 214°–215° C.

Anal. calc'd for $C_{23}H_{20}ClFN_2O_7S$: C, 52.83; H, 3.85; N, 5.26. Found: C, 53.17; H 3.72; N, 5.10.

EXAMPLE 81

6-Chloro-5-fluoro-2,3-dihydro-3-[trans-1-carboxy-2-cyploroylcarbonylmethoxy-(2-thienyl)methylene]2-oxo-1H-indole-1-carboxamide methane sulfonic acid salt a) The 1-N-t-BOC-cyclopropanoyl derivative of the title compound was prepared in the same manner as described in Example 73, Step c). Crystallization from ether gave a yellow solid, 780 mg (4.4%): M.P. 179°–180° C.

Anal. calc'd for $C_{24}H_{23}ClFN_3O_7S$: C, 52.22; H, 4.20; N, 7.61. Found: C, 52.30; H, 4.03; N, 7.67.

b) The title compound was prepared in the same manner as described in Example 73. Crystallization from methanol gave a yellow solid, 235 mg (78%): M.P. 175°–182° C. Amorphous solid.

Anal. calc'd for $C_{19}H_{15}ClFN_3O_5S \bullet CH_3SO_3H \bullet \frac{1}{2}H_2O$: C, 43.13; H, 3.62; N, 7.54. Found: C, 43.17; H, 3.33; N, 7.46.

EXAMPLE 82

6-Chloro-5-fluoro-2,3-dihydro-3-[trans-1-carboxy-2-cyclopropylcarbonylmethoxy-(2-thienyl)methylene]-2-oxo-1H-indole-1-carboxamide a) To a solution of sodium hydroxide (12.0 g, 0.3 mole) and water (200 ml) was added diethyl-1-2-cyclopanedicarboxylate (18.6 g, 0.10 mole) and stirred at 80° C. for 5 hr. The solution was evaporated to a solid with cooling (0°–5° C.). Concentrated hydrochloric acid (50 ml), was added slowly with cooling then heated on a steam bath, filtered the insolubles, and cooled in an ice-water bath. The resultant crystals were collected and dissolved in acetone and evaporated to afford the trans-1,2-cyclopanedicarboxylic acid, 6.2 g (47.6%): M.P. 176°–177° C. Lit. Ref.: JACS 4994–4999 (1957) M.P. 176°–177° C.

b) A mixture of trans-1,2-cyclopropanedicarboxylic acid (3.0 g, 0.0231 mole) and thionyl chloride (20 ml) was refluxed for 1.5 hr, then cooled and evaporated to yield an oil. The oil was dissolved in benzene (20 ml) and 2-(trimethylsilyl) ethanol (2.13 g, 0.018 mole), was added slowly and then stirred overnight at room temperature. The reaction mixture was filtered and evaporated to yield the crude product as a light brown oil 3.96 g (42%).

c) The 6-chloro-5-fluoro-2,3-dihydro-2-[trans-1-(2-trimethylsilyoxycarbonyl)-2-(cyclopanoyl)-oxy-(2-thienyl)methylene]-2-oxo-1H-indole-1-carboxamide(Z-)isomer was prepared in the same manner as described in Example 54 with the exception that it was separated on a silica gel pad and eluted with hexane and ethyl acetate (4:1) to give the crude product. Crystallization from chloroform and hexane gave a yellow solid, 140 mg (3.7%): M.P. 181°–182° C.

Anal. cal'd for $C_{24}H_{24}ClFN_2O_6SSi$: C, 52.31; H, 4.39; N, 5.08. Found: C, 52.32; H, 4.36; N, 5.12.

d) The E isomer was isolated as in the same manner as described in Step c). Crystallization from chloroform and hexane gave a yellow solid, 160 mg (4.2%): M.P. 175°–176° C. CP-152,775.

Anal. calc'd for $C_{24}H_{24}ClFN_2O_6SSi$: C, 52.31; H, 4.39; N, 5.08. Found: C, 52.45; H, 4.28; N, 4.92.

e) A suspension of the trimethylsiloxycyclopropyl derivative of the title compound (800 mg, 1.45 mmole), in hydrogen fluoride-pyridine complex (5 ml) at (−20° C.) was stirred for 30 min, added 20 ml of water and filtered the crude solids. Crystallization from ether gave a yellow solid, 412 mg (61.7%): M.P. 195° C. dec.

Anal. Calc'd for $C_{19}H_{12}ClFN_2O_6S \cdot \frac{1}{2}H_2O$: C, 49.63; H, 2.85; N, 6.09. Found: C, 49.81; H, 2.62; N, 6.06.

EXAMPLE 83

6-Chloro-5-fluoro-2,3-dihydro-3-[1,3-dioxane-5-carbonylmethoxy-(2-thienyl)methylene]-2-oxo-1H-indole-1-carboxamide a) The 1,3-dioxane-5-carboxylic acid was synthesized as described in Synthesis Communications 23 (1974).

b) The chloromethyl ester was prepared in the same manner as described in Example 73, Step c). Yielded a light yellow oil, 4.3 g (48%).

c) The 1,3-dioxane derivative, was prepared in the same manner as for the preparation of Example 73. Isolation from a silica gel column (42×5.5 cm) that was eluted with hexane and ethyl acetate (7:1) was evaporated in vacuo to yield the product as a yellow solid, 150 mg (1.3%): M.P. 199°-200° C.

Anal. calc'd for $C_{20}H_{16}ClFN_2O_7S$: C, 49.75; H, 3.34; N, 5.80. Found: C, 49.84; H, 3.17; N, 5.8.

EXAMPLE 84

6-Chloro-5-fluoro-2,3-dihydro-3-[1-(4-methoxybenzyloxycarbonyl)-5-(3-methyl)pentoylmethoxy-(2-thienyl)methylene]-2-oxo-1H-indole-1-carboxamide a) The chloromethyl ester was prepared in the same manner as described in the synthesis of Example 73, Step b). The product was isolated as an oil 9.92 g (26%). Used directly in the next step.

The title compound was prepared in the same manner as Example 76. Crystallization from ether gave an orange solid, 150 mg (7.6%): M.P. 113°-114° C.

Anal. calc'd for $C_{29}H_{26}ClFN_2O_8S$: C, 56.45; H, 4.25; N, 4.54. Found: C, 56.32; H, 4.13; N, 4.56.

PREPARATION 1—METHYL (1-CHLOROETHOXY)CARBONYLOXYACETATE

To an ice-water bath cooled solution of methyl glycolate (13.5 mL) and N,N-diisopropylethylamine (30.46 mL) in tetrahydrofuran (180 mL) was added dropwise with stirring 25.0 g of 1-chloroethyl chloroformate. The 0° C. bath was removed, and the mixture stirred for an additional 3 hr. After filtration to remove insoluble amine hydrochloride, the THF solution was evaporated under reduced pressure. The residue was dissolved in a mixture of ethyl acetate and water. The ethyl acetate layer was separated, dried over anh. sodium sulfate, and evaporated under reduced pressure to give 31.1 g of reddish oil. NMR.

PREPARATION 2—METHYL (1-IODOETHOXY)CARBONYLOXYACETATE

Sodium iodide (13.19 g), acetone (35 mL), and methyl (1-chloroethoxy)carbonyloxyacetate (8.65 g) were heated to reflux for 2.5 hr. After cooling, the mixture was filtered, and the filtrate evaporated in vacuo to a brownish oil. N-methylmorpholine (1.2 mL) and 5.8 mL of the brownish oil were dissolved in 50 mL of methylene chloride, and the mixture stirred at room temperature for 45 min. After filtration, the methylene chloride solution was evaporated, and ethyl acetate and water added to the residue. The ethyl acetate phase was separated, dried over anh. sodium sulfate, and evaporated to provide 2.18 g of crude product, containing about 68% methyl (1-iodoethoxy)carbonyloxyacetate and about 32% methyl (1-chloroethoxy)carbonyloxyacetate. This crude product was used without further purification.

PREPARATION 3—N,N-DIMETHYLGLYCOLAMIDE

To a solution of dimethylamine (25.52 g) in 150 mL of methanol was added 14.8 g of methyl glycolate, and the mixture allowed to stand at 20° C. for 18 hr. Excess dimethylamine and methanol were evaporated under reduced pressure, and ethyl ether added to the residue to cause crystallization. White crystals (13.15 g) melting at 44°-46° C. were obtained after filtration and drying.

PREPARATION 4—N,N-DIMETHYL-(1-CHLOROETHOXY)CARBONYLOXYACETAMIDE

To an ice-water bath cooled solution of N,N-dimethylglycolamide (15.64 g) and N,N-diisopropylethylamine (26.4 mL) in tetrahydrofuran (100 mL) was added dropwise with stirring 16.37 mL of 1-chloroethyl chloroformate. The 0° C. bath was removed, and the mixture stirred for an additional 4 hr. After filtration to remove insoluble amine hydrochloride, the THF solution was evaporated under reduced pressure to leave 25.5 g of brown solids. The crude product was slurried in petroleum ether, filtered, and dried in vacuo to give 19.98 g of off-white solids, mp 59°-60.8° C.

PREPARATION 5—N,N-DIMETHYL-(1-IODOETHOXY)CARBONYLOXYACETAMIDE

Sodium iodide (17.16 g), acetone (35 mL), and N,N-dimethyl-(1-chloroethoxy)carbonyloxyacetamide (12.0 g) were heated to reflux for 1.5 hr. After cooling, the mixture was filtered, and the filtrate evaporated. Ethyl acetate was added to the residue and insolubles filtered off. After evaporation of the ethyl acetate, chloroform was added and insolubles filtered off. Evaporation of the chloroform solution gave 13.0 g of reddish oil. Ethyl ether was added to the residue and the ether soluble portion was decanted from the ether insolubles. Evaporation of the ether solution gave 4.0 g of a yellow-orange oil. Methylene chloride (30 mL) and 0.42 mL of N-methylmorpholine were added to the yellow-orange oil, and the mixture stirred at room temperature for 45 min., then concentrated in vacuo. The residue was distributed between ethyl acetate and water, and the ethyl acetate layer separated, dried over sodium sulfate, and evaporated under reduced pressure to give 2.55 g of yellow solid, shown by nmr to be about 66% N,N-dimethyl-(1-iodoethoxy)carbonyloxyacetamide and about 33% N,N-dimethyl-(1-chloroethoxy)carbonyloxyacetamide. This crude material was used without further purification.

PREPARATION 6—N,N-DIETHYLGLYCOLAMIDE

To a 0° C. solution of diethylamine (1819 mL) and triethylamine (25.5 mL) in 500 mL of methylene chloride was added dropwise, with stirring, 25 g of acetoxyacetyl chloride. The ice bath was removed, and the mixture allowed to warm to 20° C. while stirring for an additional 2 hr. After filtration to remove amine hydrochloride salts, the methylene chloride solution was evaporated under reduced pressure to provide 29.1 g of crude, N,N-diethylacetoxyacetamide, as a yellow oil. The yellow oil was dissolved in 125 mL of methanol and 168 mL of 1N sodium hydroxide added with stirring. A slight exotherm was noted, and the mixture was allowed to stir for 2 hr. without further warming. Solvents were removed under reduced pressure to ¼ volume, and the remaining aqueous solution extracted with ethyl acetate (200 ml). The ethyl acetate extract was dried over anh. sodium sulfate, and evaporated under reduced pressure to provide 14.0 g of N,N-diethylglycolamide as a yellow oil.

PREPARATION 7—N,N-DIETHYL-(1-CHLOROETHOXY)CARBONYLOXYACETAMIDE

To an ice-water bath cooled solution of N,N-diethylglycolamide (19.25 g) and N,N-diisopropylethylamine (26.2 mL) in tetrahydrofuran (100 mL) was added dropwise with stirring 15.8 mL of 1-chloroethyl chloroformate. The ice bath was removed, and the mixture stirred for an additional 4 hr. After filtration to remove insoluble amine hydrochloride, the THF solution was evaporated under reduced pressure. The solid residue was dissolved in ethyl acetate and the solution washed with water, dried over anh. sodium sulfate, and evaporated to a solid residue. After slurrying in ethyl ether, the solid was filtered and dried to give 18.4 g of off-white crystals melting at 76°-78° C.

PREPARATION 8—N,N-DIETHYL-(1-IODOETHOXY)CARBONYLOXYACETAMIDE

Sodium iodide (15.14 g), acetone (35 mL), and N,N-diethyl-(1-chloroethoxy)carbonyloxyacetamide (12.0 g) were heated to reflux for 1.5 hr. After cooling, the mixture was filtered, and the filtrate evaporated. Ethyl acetate and water were added to the residue with stirring. The ethyl acetate layer was separated, dried over anh. sodium sulfate, and evaporated in vacuo to give 13.6 g of reddish solid, which was shown by nmr to be about 58% N,N-diethyl-(1-iodoethoxy)carbonyloxyacetamide and about 42% N,N-diethyl-(1-chloroethoxy)carbonyloxyacetamide. The material was used without further purification.

PREPARATION 9—DIMETHYLAMMONIUM N,N-DIMETHYLSUCCINAMATE

Dimethylamine gas was bubbled slowly for 1 hr. into a precooled (0° C.) mixture of succinic anhydride (10 g) and tetahydrofuran (75 mL). The cooling bath was removed, and the reaction mixture stirred an additional 30 min., then evaporated under reduced pressure to give 17.57 g of clear oil.

PREPARATION 10—CHLOROMETHYL N,N-DIMETHYLSUCCINAMATE

To 50 mL of methylene chloride was added, with stirring, 10 ml of water, 31.4 g of tetrabutylammonium hydrogen sulfate, 92.5 mL of 1N sodium hydroxide, and 17.57 g of dimethylammonium N,N-dimethylsuccinamate dissolved in 50 mL of methylene chloride. After stirring for 2.25 hr., the methylene chloride layer was separated, dried over anh. sodium sulfate, and evaporated in vacuo to give 26.8 g of oil. The oil was dissolved in 100 mL of bromochloromethane and stirred at 20° C. for 17 hr. After evaporation of the bromochloromethane in vacuo, the residual oil was extracted with ethyl ether several times. The ether extracts were combined and evaporated to give 5.4 g of oil. The crude product was purified by chromatography on silica gel using 70:30 chloroform-ethyl acetate. Fractions containing the desired product were combined and concentrated to give 2.3 g of clear oil.

PREPARATION 11—IODOMETHYL N,N-DIMETHYLSUCCINAMATE

Sodium iodide (3.57 g) was added to a solution of chloromethyl N,N-dimethylsuccinamate (2.3 g) in 10 mL acetone, and the mixture stirred at 20° C. for 2 hr. After evaporation of the solvent in vacuo, the residue was dissolved in a mixture of methylene chloride and water. The methylene chloride layer was separated, dried over anh. sodium sulfate, and evaporated to give 3.27 g of a brownish oil, which was used without further purification.

PREPARATION 12—CHLOROMETHYL N,N-DIETHYLSUCCINAMATE

Tetrabutylammonium hydrogen sulfate (19.6 g), N,N-diethyl succinamic acid (10.0 g), sodium bicarbonate (4.85 g) and 1N sodium hydroxide (58 mL) were combined in 400 mL methylene chloride and 80 mL water with stirring. After 1.5 hr., the phases were separated. The methylene chloride layer was dried over anh. sodium sulfate and evaporated under reduced pressure to give 9.6 g of oil. The aqueous layer was extracted with additional methylene chloride, and an additional 4.2 g of oil was obtained after solvent drying and evaporation. A portion (4.2 g) of this oily tetrabutylammonium salt was dissolved in 100 mL of bromochloromethane and the solution was allowed to stir at 20° C. for 40 hr. After evaporation of the bromochloromethane in vacuo, the residue was repeatedly extracted with ethyl ether. The combined ethyl ether extracts were evaporated to 2.3 g of clear oil. The oil was purified by chromatography on silica gel, with elution by 80:20 chloroform-ethyl acetate to give 1.62 g of oil.

PREPARATION 13—IODOMETHYL N,N-DIETHYLSUCCINAMATE

Sodium iodide (2.19 g) and chloromethyl N,N-diethylsuccinamate (1.62 g) were combined with 15 mL acetone, and the mixture stirred at 20° C. for 3 hr. Solvent was evaporated in vacuo, and the residue distributed between methylene chloride and water. The methylene chloride layer was separated, dried over anh. sodium sulfate, and evaporated under reduced pressure to give 1.81 g of oil which was used without further purification.

PREPARATION 14—DIPROPYLAMMONIUM N,N-DIPROPYLSUCCINAMATE

Succinic anhydride (15.0 g) was added to a precooled (0° C.) solution of dipropylamine (41 mL) in 200 mL methanol. The cooling bath was removed and the mixture stirred for 30 min. before solvent evaporation to give 42.8 g of pale yellow oil.

PREPARATION 15—CHLOROMETHYL N,N-DIPROPYLSUCCINAMATE

A mixture containing dipropylammonium N,N-dipropylsuccinamate (41.8 g), tetrabutylammonium hydrogen sulfate (48.05 g), methylene chloride (250 mL), water (80 mL), and 1N sodium hydroxide (142 mL) was stirred for 1.5 hr. The methylene chloride layer was separated, dried over anh. sodium sulfate, and evaporated in vacuo to give 44.12 g of oil. Twenty grams of this oil was dissolved in 100 mL of bromochloromethane, and the solution stirred for 4.5 hr. Bromochloromethane was evaporated in vacuo. The residue was extracted several times with ethyl ether, and the ether extracts combined and evaporated to give 6.5 g of yellow oil, which was used without further purification.

PREPARATION 16—IODOMETHYL N,N-DIPROPYLSUCCINAMATE

Sodium iodide (7.8 g) was added to a solution of chloromethyl N,N-dipropylsuccinamate (6.5 g) in 30 mL acetone, and the mixture stirred for 2.5 hr. After evaporation of the solvent in vacuo, the residue was dissolved in a mixture of methylene chloride and water. The methylene chloride layer was separated, dried over anh. sodium sulfate, and evaporated to give 8.8 g of orange oil, which was used without further purification.

PREPARATION 17—HOMOPIPERIDINIUM 4-HOMOPIPERIDINO-4-OXOBUTYRATE

Succinic anhydride (15.0 g) was added carefully to a solution of homopiperidine (33.78 mL) in tetrahydrofuran (100 mL), and the mixture allowed to stir for 30 min. The solvent was evaporated in vacuo to give 33.16 g of oil.

PREPARATION 18—CHLOROMETHYL 4-HOMOPIPERIDINO-4-OXOBUTYRATE

A mixture of homopiperidinium 4-homopiperidino-4-oxobutyrate (33.16 g), tetrabutylammonium hydrogen sulfate (49.74 g), methylene chloride (200 mL), water (50 mL), and 1N sodium hydroxide (146 mL) was stirred for 1.5 hr. The methylene chloride phase was separated, dried over anh. sodium sulfate, and evaporated in vacuo to give 22.0 g of a clear oil. The oil was dissolved in 100 mL of bromochloromethane and stirred for 17 hr. at 20° C. After in vacuo evaporation of the bromochloromethane, the residue was extracted with ethyl ether. The ether solution was dried over sodium sulfate and evaporated in vacuo to give 10.5 g of oil. This oil was purified by chromatography on silica gel using 85:15 chloroform-ethyl acetate as eluant. Fractions containing the desired chloromethyl ester were combined and evaporated to give 4.36 g of clear oil.

PREPARATION 19—IODOMETHYL 4-HOMOPIPERIDINO-4-OXOBUTYRATE

Sodium iodide (5.28 g) was added to a solution of chloromethyl 4-homopiperidino-4-oxobutyrate (4.36 g) in 20 mL of acetone, and the mixture stirred for 3 hr. The solvent was evaporated in vacuo, and the residue distributed between water and methylene chloride. The methylene chloride layer was separated, dried over anh. sodium sulfate, and evaporated in vacuo to give 4.4 g of yellow oil, which was used without further purification.

PREPARATION 20—METHYL N,N-DIMETHYLAMINOCARBONYLOXYACETATE

Pyridine (67 mL), methyl glycolate (12.85 mL), and dimethylcarbamyl chloride (15.33 mL) were combined at 0° C., then the cooling bath removed, and the solution allowed to stir at 20° C. for 17 hr. The reaction mixture was then heated at 65° C. for 4 hr. cooled, ethyl acetate and water added, and the mixture was made acidic by the addition of 1N HCl. The ethyl acetate layer was separated, washed with brine, dried over anh. sodium sulfate, and concentrated in vacuo to give 7.1 g of yellow oil. The residue was chromatographed on silica gel with chloroform as eluant. Collection tubes determined to contain the desired product were combined and concentrated to give 2.5 g of oil.

PREPARATION 21—N,N-DIMETHYLAMINOCARBONYLOXYACETIC ACID, SODIUM SALT

The ester described above (2.5 g) was dissolved in 10 mL methanol, 1N sodium hydroxide (15.5 mL) added, and the solution allowed to stir at 20° C. for 1 hr. Evaporation of the reaction mixture under reduced pressure provided a white soid that was used without further purification.

PREPARATION 22—CHLOROMETHYL N,N-DIMETHYLAMINOCARBONYLOXYACETATE

The N,N-dimethylaminocarbonyloxyacetic acid sodium salt (2.62 g) was combined with 100 mL methylene chloride, 30 mL water, 5.27 g of tetrabutylammonium hydrogen sulfate and 1.3 g of sodium becarbonate and stirred for 1.5 hr. The methylene chloride layer was removed, dried over anh. sodium sulfate, and evaporated in vacuo to provide 2.8 g of oil. The oil was dissolved in 80 mL of bromochloromethane and stirred at 20° C. for 18 hr. The methylene chloride was evaporated in vacuo and the residue extracted several times with ethyl ether. The extracts were combined and evaporated to give 0.95 g of oil, which was used without further purification.

PREPARATION 23—IODOMETHYL N,N-DIMETHYLAMINOCARBONYLOXYACETATE

Sodium iodide (1.46 g) and chloromethyl N,N-dimethylaminocarbonyloxyacetate (0.95 g) were combined with 30 mL of acetone, and stirred at 20° C. for 19 hr. The acetone was evaporated in vacuo to give 1.18 g of oil, which was used without further purification.

PREPARATION 24—METHYL N,N-DIETHYLAMINOCARBONYLOXYACETATE

Pyridine (54 mL), methyl glycolate (10.3 mL), and diethylcarbamyl chloride (16.9 mL) were combined, heated for 40 hr. at 65° C., for an additional 24 hr. at 85° C., and an additional 24 hr. at 95° C. After cooling, the reaction mixture was distributed between ethyl acetate and water. The ethyl acetate layer was separated, washed with 1N HCl, water, and brine, dried over anh. sodium sulfate, and concentrated in vacuo to give 15.0 g of oil which was used without further purification.

PREPARATION 25—N,N-DIETHYLAMINOCARBONYLOXYACETIC ACID, SODIUM SALT

The ester described above (15 g) was dissolved in 100 mL methanol, 1N sodium hydroxide (79.3 mL) added, and the solution allowed to stir at 20° C. for 1.5 hr. Evaporation of the reaction mixture under reduced pressure provided a white solid, 15.3 g after drying of $P_2O_5$, that was used without further purification.

PREPARATION 26—IODOMETHYL N,N-DIETHYLAMINOCARBONYLOXYACETATE

N,N-Diethylaminocarbonyloxyacetic acid sodium salt (15.3 g) was combined with 800 mL methylene chloride, 240 mL water, 26.35 g of tetrabutylammonium hydrogen sulfate and 6.52 g of sodium bicarbonate and stirred for 1.5 hr. The methylene chloride layer was removed, dried over anh. sodium sulfate, and evaporated in vacuo and the residue extracted several times with ethyl ether. The extracts were combined and evaporated to give 10.63 g of oil. This crude chloromethyl ester was combined with sodium iodide (14.25 g) in 100 mL of acetone and stirred at 20° C. for 3.5 hr. Solvent was evaporated in vacuo, and the residue distributed between chloroform and water. The chloroform layer was dried over anh. sodium sulfate and evaporated in vacuo to give 11.56 g of light yellow oil that was used without further purification.

PREPARATION 27—ETHYL N-PIVALOYLGLYCINATE

To a stirred, ice-bath cooled flask containing 150 mL of methylene chloride were added ethyl glycinate hydrochloride (25.0 g), pivaloyl chloride (20.9 mL) and, slowly, 62.4 mL of N,N-diisopropylethylamine. After removal of the ice bath, the reaction solution was stirred for 4 hr. Solvent was evaporated in vacuo and the residual oil distributed between added ethyl acetate and water. The ethyl acetate layer was washed with a 1:1 mixture of sat. aq. sodium bicarbonate and water, dried over anh. sodium sulfate, and evaporated in vacuo to give 11.3 g of oil.

PREPARATION 28—SODIUM N-PIVALOYLGLYCINATE

To a solution of ethyl N-pivaloylglycinate (11.3 g) in 50 mL of methanol was added 69.2 mL of 1N sodium hydroxide, and the solution stirred for 2 hr. Solvents were evaporated in vacuo. Fresh methanol was added and reevaporated to give 12.45 g of off-white solid.

PREPARATION 29—CHLOROMETHYL N-PIVALOYLGLYCINATE

To a stirred solution of sodium N-pivaloylglycinate (12.45 g) and tetrabutylammonium hydrogen sulfate (21.8 g) in 100 mL methylene chloride and 50 mL water was added 64.3 mL 1N sodium hydroxide, and the mixture stirred for 3 hr. The methylene chloride layer was separated, dried over sodium sulfate, and evaporated in vacuo to give 20.9 g of oil. The oil was dissolved in 50 mL of bromochloromethane and stirred for 17 hr. at 20° C. After evaporation of the bromochloromethane, the residue was repeatedly extracted with ethyl ether. The combined extracts were evaporated in vacuo to give 2.2 g of oil. Chromatography on silica gel with chloroform-ethyl acetate elution gave 1.2 g of the chloromethyl ester.

PREPARATION 30—IODOMETHYL N-PIVALOYLGLYCINATE

A mixture of sodium iodide (1.71 g), chloromethyl N-pivaloylglycinate (1.2 g) and acetone (20 mL) was stirred at 20° C. for 19 hr. The solvent was evaporated in vacuo and the residue distributed between added chloroform and water. The phases were separated and the water layer reextracted with chloroform. The chloroform layers were combined, dried over anh. sodium sulfate, and evaporated in vacuo to give 1.45 g of oil. This material was used without further purification.

PREPARATION 31—ETHYL N-(2-ETHYLBUTYRYL)GLYCINATE

To a stirred, ice-bath cooled flask containing 200 mL of methylene chloride were added ethyl glycinate hydrochloride (25.0), 2-ethylbutyric anhydride (39.3 mL) and, slowly, 54.8 mL of triethylamine. After removal of the ice bath, the reaction solution was stirred for 17 hr. Solvent was evaporated in vacuo and the residue distributed between added ethyl acetate and water. The ethyl acetate layer was washed with a 1:1 mixture of saturated aqueous sodium bicarbonate and water, dried over anh. sodium sulfate, and evaporated in vacuo to give 33.73 g of white fluffy solid.

PREPARATION 32—SODIUM N-(2-ETHYLBUTYRYL)GLYCINATE

To a solution of ethyl N-(2-ethylbutyryl)glycinate (33.73 g) in 100 mL of methanol was added 167.6 mL of 1N sodium hydroxide, and the solution stirred for 1.5 hr. Solvents were evaporated in vacuo, and then fresh methanol was added and evaporated to give 32.6 g of a pale yellow oil.

PREPARATION 33—CHLOROMETHYL N-(2-ETHYOLBUTYRYL)GLYCINATE

To a stirred solution of sodium N-(2-ethylbutyryl)-glycinate (32.6 g) and tetrabutylammonium hydrogen sulfate (53.3 g) in 100 mL methylene chloride and 100 mL water was added 157 mL of 1N sodium hydroxide, and the mixture stirred for 2.5 hr. The phases were separated, and the aqueous layer reextracted with 400 mL methylene chloride. The organic layers were combined, dried over sodium sulfate, and evaporated in vacuo to give 59.8 g of oil. The oil was dissolved in 75 mL of bromochloromethane and stirred for 15 hr. at 20° C. After evaporation of the bromochloromethane, the residue was repeatedly extracted with ethyl ether. The combined extracts were evaporated in vacuo to give 7.84 g of oil. Chromatography on silica gel with chloroform-ethyl acetate (3:1) elution gave 2.33 g of the chloromethyl ester.

PREPARATION 34—IODOMETHYL N-(2-ETHYLBUTYRYL)GLYCINATE

A mixture of sodium iodide (3.15 g), chloromethyl N-(2-ethylbutyrl)glycinate (2.33 g) and acetone (20 mL) was stirred at 20° C. for 17 hr. The solvent was evaporated in vacuo and the residue distributed between added methylene chloride and water. The phases were separated and the water layer reextracted twice with methylene chloride. The organic extracts were combined, dried over anh. sodium sulfate, and evaporated in vacuo to give 2.78 g of solid. This material was used without further purification.

PREPARATION 35—1-IODOETHYL ISOPROPYL CARBONATE

1-Chloroethyl chloroformate was converted to 1-iodoethyl isopropyl carbonate using the procedure given by Wan-Joo Kim, et al, The Journal of Antibiotics, (1991) 44, pg. 1086.

| HALOALKYL ESTER INTERMEDIATES | | | | |
|---|---|---|---|---|
| Preparation | $R^1$ | $R^2$ | $R^3$ | $^1$H NMR Date (CDCl$_3$), $\delta$ |
| 1 | Me | OCH$_2$CO$_2$Me | Cl | 1.83(d, 3H); 3.77(s, 3H); 4.67(ABq, 2H); 6.40 (q, 1H). |
| 4 | Me | OCH$_2$CONMe$_2$ | Cl | 1.86(d, 3H); 2.97(s, 3H); 2.99(s, 3H); 2.99(s, 3H); 4.68(d, 1H); 4.90(d, 1H); 6.45(q, 1H). |
| 7 | Me | OCH$_2$CONEt$_2$ | Cl | 1.10(t, 3H); 1.19(t, 3H); 1.81(d, 3H); 3.18(q, 2H); 3.37(q, 2H); 4.64(d, 1H); 4.86(d, 1H); 6.41(q, 1H). |
| 10 | H | CH$_2$CH$_2$CONMe$_2$ | Cl | 2.62-2.78(m, 4H); 2.96(s, 3H); 3.04(s, 3H); 5.72(s, 2H). |
| 11 | H | CH$_2$CH$_2$CONMe$_2$ | I | 2.67(s, 4H); 2.96(s, 3H); 3.03(s, 3H); 5.93(s, 2H). |
| 12 | H | CH$_2$CH$_2$CONEt$_2$ | Cl | 1.02(t, 3H); 1.14(t, 3H); 2.54-2.71(m, 4H); 3.21-3.38(m, 4H); 5.84(s, 2H). |
| 13 | H | CH$_2$CH$_2$CONEt$_2$ | I | 1.14(t, 3H); 1.24(t, 3H); 2.68-2.81(m, 4H); 3.32-3.50(m, 4H); 5.92(s, 2H). |
| 15 | H | CH$_2$CH$_2$CONPr$_2$ | Cl | 0.86(t, 3H); 0.94(t, 3H); 1.44-1.78(m, 4H); 2.60-2.84(m, 4H); 3.16-3.40(m, 4H); 5.72(s, 2H). |
| 19 | H | (CH$_2$)$_2$CON(CH$_2$)$_6$ | I | 1.50-1.90(m, 8H); 2.65-2.80(m, 4H); 3.44-3.64(m, 4H); 5.93 (s, 2H). |
| 22 | H | CH$_2$OCONMe$_2$ | Cl | 2.92(s, 3H); 2.95(s, 3H); 4.63(s, 2H); 5.73(s, 2H). |
| 23 | H | CH$_2$OCONMe$_2$ | I | 2.96(s, 3h); 2.99(s, 3H); 4.61(s, 2H); 5.95(s, 2H). |
| 26 | H | CH$_2$OCONEt$_2$ | Cl | 1.12-1.23(m, 6H); 3.27-3.38(m, 4H); 4.70(s, 2H); 5.76(s, 2H). |
| 29 | H | CH$_2$NHCOCMe$_3$ | Cl | 1.24(s, 9H); 4.12(d, 2H); 5.75(s, 2H); 6.15(br. s, 1H). |
| 30 | H | CH$_2$NHCOCMe$_3$ | I | 1.25(s, 9H); 4.06(d, 2h); 5.96(s, 2H); 6.15(br. s, 1H). |
| 34 | H | CH$_2$NHCOCHEt$_2$ | I | 0.93(t, 6H); 1.44-1.75(m, 4H); 1.92-2.10(m, 1H); 4.10(ABq, 2H); 5.93(br. s, 1H); 5.96(s, 2H). |

We claim:
1. A compound of the formula:

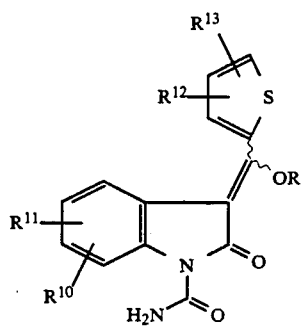

I wherein R is

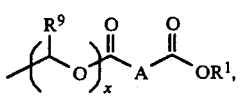

II

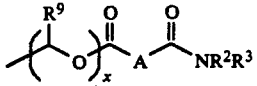

III

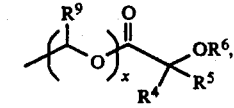

IV

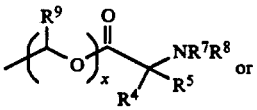

V

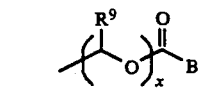

VI wherein x is 0 or 1;

A is a C$_1$-C$_5$ alkylene or C$_2$-C$_6$ alkenyl chain, optionally substituted with up to two substituents independently selected from C$_1$-C$_7$ alkyl or C$_3$-C$_7$ cycloalkyl; or (CH$_2$)$_n$O(CH$_2$)$_m$, where the methylene groups may be optionally substituted with up to two substituents independently selected from C$_1$-C$_7$ alkyl or C$_3$-C$_7$ cycloalkyl; or a C$_3$-C$_7$ cycloalkyl or cycloalkenyl group optionally substituted with up to two C$_1$-C$_3$ alkyl groups; or a 4-7 membered hetero-alicyclic group containing an O, S or NR$^6$ link; or a phenylene group optionally substituted with up to two substituents independently selected from C$_1$-C$_3$ alkyl, C$_1$-C$_3$ alkyloxy, halogen or CF$_3$;

B is C$_2$-C$_6$ alkenyl phenyl, 2,3 or 4-pyridyl, 2,3 or 4-piperidinyl, 2- or 3-pyrrolidinyl, —OCH$_2$CO$_2$R$^1$ or —OCH$_2$CONR$^2$R$^3$;

R$^1$ is H, C$_1$-C$_8$ alkyl, C$_3$-C$_7$ cycloalkyl, phenyl(C$_1$-C$_4$)alkyl, (CH$_2$)$_p$CO$_2$R$^2$, or (CH$_2$)$_p$CONR$^2$R$^3$, (CH$_2$)$_p$Si(CH$_3$)$_2$; or R$^1$ may form with A a 5,6 or 7 membered lactone ring optionally substituted with a C$_1$-C$_3$alkyl group.

R$^2$ and R$^3$ are independently H, C$_1$-C$_7$ alkyl, C$_3$-C$_7$ cycloalkyl, phenyl(C$_1$-C$_4$)alkyl; or R$^2$ and R$^3$, when taken together with the attached nitrogen, may represent a pyrrolidine, piperidine, morpholine or homopiperidine group optionally substituted with up to two C$_1$-C$_3$ groups; or R$^2$ or R$^3$ may form with A, a 5,6 or 7 membered lactam ring, optionally substituted with up to two C$_1$-C$_3$ alkyl groups;

R$^4$ and R$^5$ are independently H, C$_1$-C$_7$ alkyl, C$_3$-C$_7$ cycloalkyl, phenyl(C$_1$-C$_4$)alkyl, (CH$_2$)$_p$CO$_2$R$^2$, (CH$_2$)$_p$CONR$^2$R$^3$, (CH$_2$)$_p$NR$^7$R$^8$, (CH$_2$)$_p$OR$^6$ or (CH$_2$)$_p$SR$^6$; or R$^4$ and R$^5$ when taken together represent a C$_3$-C$_7$ cycloalkyl ring, optionally substituted with up to two C$_1$C$_3$ alkyl groups;

R$^6$ is H, C$_1$-C$_6$ alkyl, (CH$_2$)$_p$COOR$^2$, C$_3$-C$_7$ cycloalkyl optionally substituted with up to two C$_1$-C$_6$ alkyl groups, phenyl(C$_1$-C$_4$)alkyl optionally substituted on the phenyl ring with up to two substituents independently selected from C$_1$-C$_3$alkyl, $C_1$–$C_3$ alkyloxy, halogen or $CF_3$, $COR^2$, $CONR^2R^3$, or a phenyl group optionally substituted with up to two substituents independently selected from $C_1$–$C_3$ alkyl, $C_1$–$C_3$ alkyloxy, halogen or $CF_3$; or when taken with $R^4$ and the attached oxygen, may represent an oxetan, tetrahydrofuran, tetrahydropyran or oxepan ring optionally substituted with up to two $C_1$–$C_3$ alkyl groups;

$R^7$ and $R^8$ are independently H, $C_1$–$C_6$ alkyl, $C_3$–$C_7$ cycloalkyl, phenyl($C_1$–$C_4$)alkyl, $COR^2$, $COOR^2$; or independently $C_2$–$C_7$ alkanoyl, $C_4$–$C_8$ cycloalkanoyl, optionally substituted with up to two substituents independently selected from $C_1$–$C_6$ alkyl, $C_3$–$C_7$ cycloalkyl, phenyl($C_1$–$C_4$)alkyl, $C_3$–$C_7$ branched alkyl; or $R^7$ and $R^8$ when taken together with the attached nitrogen may represent a pyrrolidine, piperidine or homopiperidine group optionally substituted with up to two substituents independently selected from $C_1$–$C_6$ alkyl, $C_3$–$C_7$ cycloalkyl, $C_3$–$C_7$ branched alkyl, or oxo;

$R^9$ is H or methyl;

$R^{10}$, $R^{11}$, $R^{12}$ and $R^{13}$ are independently selected from hydrogen, $C_1$–$C_4$ alkyl and halogen; m and n are independently 0, 1 or 2 where either m or n must be at least $=1$; and p is 1 to 3;

and with the proviso that when R is the structure of Formula II, and x is 0;

A must be a group other than $C_2$–$C_6$ alkylene.

2. A compound of claim 1, wherein one of $R^{10}$ and $R^{11}$ is 5-fluoro and the other is 6-chloro.

3. A compound of claim 2, wherein R is

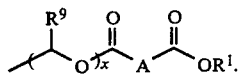

4. A compound of claim 3 wherein x is 0.

5. A compound of claim 4 wherein A is a $C_2$–$C_6$ alkenyl chain and $R^1$ is hydrogen.

6. A compound of claim 5 wherein $R^{12}$ and $R^{13}$ are hydrogen.

7. A compound of claim 3 wherein x is 1.

8. A compound of claim 7 wherein A is $C_1$–$C_5$ alkylene.

9. A compound of claim 8 wherein $R^1$ is benzyl.

10. A compound of claim 2 wherein R is

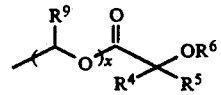

and x is 1.

11. A compound of claim 10 wherein $R^4$, $R^9$, $R^{12}$ and $R^{13}$ are hydrogen, $R^5$ is hydrogen, methyl or ethyl and $R^6$ is hydrogen, methyl, benzyl or $CH_2COOR^3$.

12. A compound of claim 2 wherein R is

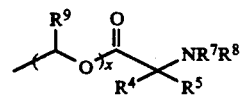

and x is 1.

13. A compound of claim 12 wherein $R^4$, $R^9$, $R^7$, $R^8$, $R^{12}$, and $R^{13}$ are hydrogen and $R^5$ is $(CH_2)_pNR^7R^8$, methyl or benzyl.

14. A compound of claim 12 wherein $R^7$ is $COR^2$.

15. A compound of claim 2 wherein R is

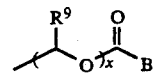

and x is 1.

16. A compound of claim 15 wherein B is 2 or 3-pyrrolidine.

17. A compound of claim 2, wherein R is

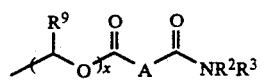

18. A method for treating inflammation in a mammal which comprises administering to said mammal an antiinflammatory effective amount of a compound selected from claim 1.

19. A method for treating pain in a mammal which comprises administering to said mammal an analgesic effective amount of a compound selected from claim 1.

20. A pharmaceutical composition comprising an analgesic or antiinflammatory effective amount of a compound of claim 1 and a pharmaceutically acceptable inert ingredient.

* * * * *